(12) United States Patent
Matsui et al.

(10) Patent No.: US 10,294,461 B2
(45) Date of Patent: May 21, 2019

(54) MODIFIED CARBONYL REDUCING ENZYME AND GENE

(71) Applicant: KANEKA CORPORATION, Osaka (JP)

(72) Inventors: Misato Matsui, Takasago (JP); Noriyuki Ito, Takasago (JP); Shigeru Kawano, Takasago (JP); Yoshihiko Yasohara, Takasago (JP)

(73) Assignee: KANEKA CORPORATION, Osaka (JP)

( * ) Notice: Subject to any disclaimer, the term of this patent is extended or adjusted under 35 U.S.C. 154(b) by 695 days.

(21) Appl. No.: 14/780,419

(22) PCT Filed: Mar. 25, 2014

(86) PCT No.: PCT/JP2014/058248
§ 371 (c)(1),
(2) Date: Sep. 25, 2015

(87) PCT Pub. No.: WO2014/157185
PCT Pub. Date: Oct. 2, 2014

(65) Prior Publication Data
US 2016/0040138 A1 Feb. 11, 2016

(30) Foreign Application Priority Data
Mar. 28, 2013 (JP) .................... 2013-070170

(51) Int. Cl.
| | |
|---|---|
| *C12N 9/02* | (2006.01) |
| *C12Q 1/26* | (2006.01) |
| *C12N 9/04* | (2006.01) |
| *C12P 7/02* | (2006.01) |
| *C12P 7/04* | (2006.01) |
| *A61K 38/00* | (2006.01) |

(52) U.S. Cl.
CPC .............. *C12N 9/0006* (2013.01); *C12P 7/02* (2013.01); *C12P 7/04* (2013.01); *C12Y 101/01184* (2013.01)

(58) Field of Classification Search
None
See application file for complete search history.

(56) References Cited

U.S. PATENT DOCUMENTS

| | | | |
|---|---|---|---|
| 2008/0233621 A1 | 9/2008 | Dekishima et al. | |
| 2009/0035828 A1* | 2/2009 | Abraham | C07K 1/1077 435/105 |
| 2009/0275083 A1* | 11/2009 | De Maria | C07K 14/37 435/69.2 |

FOREIGN PATENT DOCUMENTS

| | | |
|---|---|---|
| CN | 1656225 A | 8/2005 |
| CN | 101407780 A | 4/2009 |
| CN | 102618513 A | 8/2012 |
| EP | 1 491 633 A1 | 12/2004 |
| EP | 2562253 A1 | 2/2013 |
| JP | 2009-225773 A | 10/2009 |
| WO | WO 2005/075651 A1 | 8/2005 |
| WO | WO 2011/090753 A2 | 7/2011 |
| WO | WO 2011/142865 A2 | 11/2011 |
| WO | WO 2012/129555 A2 | 9/2012 |

OTHER PUBLICATIONS

NCBI (2008) hypothetical protein Kpol_1030p19 [Vanderwaltozyma polyspora DSM 70294], pp. 1-2.*
Shankar et al. (2010) Immobilization of intracellular carbonyl reductase from Geotrichum candidum for the stereoselective reduction of 1-naphthyl ketone, Bioresource Technol., vol. 101 , pp. 1581-1586.*
Chen et al. (2014) A Novel Carbonyl Reductase with Anti-Prelog Stereospecificity from *Acetobacter* sp. CCTCC M209061: Purification and Characterization, PLOS, vol. 9, e94543, pp. 1-12.*
Argueso et al., "Genome structure of *Saccharomyces cerevisiae* strain widely used in bioethanol production," Genome Research (2009), vol. 19, pp. 2258-2270.
English translation of International Preliminary Report on Patentability and Written Opinion dated Sep. 29, 2015, in PCT International Application No. PCT/JP2014/058248.
Goretti et al., "Production of Flavours and Fragrances via Bioreduction of (4R)-(-)-Carvone and (1R)-(-)Myrtenal by Non-Conventional Yeast Whole-Cells," Molecules (2013), vol. 18, pp. 5736-5748.
Lavandera et al., "An Exceptionally DMSO-Tolerant Alcohol Dehydrogenase for the Stereoselective Reduction of Ketones," ChemSusChem (2008), vol. 1, pp. 431-436.
NCBI Reference Sequence: XP 001644269.1 (Scannell et al., "Independent sorting-out of thousands of duplicated gene pairs in two yeast species descended from a whole-genome duplication," Proc. Natl. Acad. Sci. U.S.A. (2007), vol. 104, No. 20, pp. 8397-8402).
"A7TMT9_VANPO," UniProt Database, Mar. 16, 2016, 1 page.
Nakamura et al., "Recent developments in asymmetric reduction of ketones with biocatalysts," Tetrahedron: Asymmetry, vol. 14, 2003, pp. 2659-2681.

(Continued)

*Primary Examiner* — Manjunath N Rao
*Assistant Examiner* — Samuel W Liu
(74) *Attorney, Agent, or Firm* — Birch, Stewart, Kolasch & Birch, LLP

(57) ABSTRACT

An object of the present invention is to modify a wild-type enzyme that is less reactive in the presence of an organic solvent to provide altered carbonyl reductases having better reactivity in the presence of the organic solvent than the wild-type enzyme, and/or to provide transformants producing such reductases. The present inventors have found altered carbonyl reductases having better reactivity in the presence of an organic solvent than the wild-type enzyme, from among a mutant enzyme library prepared by randomly mutating the wild-type enzyme gene, thereby arriving at completion of the present invention.

7 Claims, No Drawings
Specification includes a Sequence Listing.

(56) References Cited

OTHER PUBLICATIONS

Salleh et al., "Modified Enzymes for Reactions in Organic Solvents," Applied Biochemistry and Biotechnology, vol. 102-103, 2002, pp. 349-357.

* cited by examiner

SEQUENCE LISTING

```
<160> NUMBER OF SEQ ID NOS: 47

<210> SEQ ID NO 1
<211> LENGTH: 335
<212> TYPE: PRT
<213> ORGANISM: Vanderwaltozyma polyspora

<400> SEQUENCE: 1

Met Ser Val Leu Val Thr Gly Ala Thr Gly Tyr Ile Ala Leu His Val
1               5                   10                  15

Ile Asp Leu Leu Leu Lys Glu Asn Tyr Arg Val Ile Gly Thr Val Arg
            20                  25                  30

Ser Lys Glu Lys Ala Ala Lys Leu Glu Lys Gln Phe Asn Tyr Asn Lys
        35                  40                  45

Asp Leu Thr Phe Glu Ile Val Glu Asp Ile Ala Asn Leu Ser Ala Phe
    50                  55                  60

Asp His Val Ile Lys Asn His Ala Asn Glu Ile Asn Tyr Val Ile His
65                  70                  75                  80

Met Ala Ser Pro Val Thr Phe Thr Ala Asp Asp Phe Glu Lys Asp Ile
                85                  90                  95

Leu Ile Pro Ala Val Asn Gly Thr Lys Gly Ile Leu Glu Ser Ile Lys
            100                 105                 110

Gln Tyr Ala Pro Lys Ser Val Lys Lys Phe Val Ile Thr Ser Ser Ile
        115                 120                 125

Ala Ala Met Met Asp Leu Thr Asn Pro Thr Ala Ile Leu Thr Glu Gln
    130                 135                 140

Ser Trp Asn Pro Thr Thr Trp Glu Gln Ala Gln Glu Asn Gly Ile Ala
145                 150                 155                 160

Ala Tyr Ser Gly Ser Lys Lys Phe Ala Glu Lys Ala Ala Trp Asn Phe
                165                 170                 175
```

Leu Glu Glu Asn Lys Gly Ile Val Asp Phe Lys Leu Thr Thr Ile Asn
            180                 185                 190

Pro Val Phe Val Phe Gly Pro Gln Lys Phe Asp Glu Asp Ala Lys Gly
        195                 200                 205

Lys Leu Asn Ser Ser Cys Glu Ile Ile Lys Glu Ala Met Phe Ala Pro
    210                 215                 220

Thr Glu Ser Glu Ile Asp Lys Ser Val Phe Gly Ser Tyr Val Asp Val
225                 230                 235                 240

Arg Asp Val Ala Arg Ala His Val Cys Ser Leu His Asn Asp Glu Leu
                245                 250                 255

Thr Gly Lys Arg Leu Ile Leu Ser Asn Ala Ser Phe Thr Lys Gln Asn
            260                 265                 270

Ile Val Asn Ile Met Asn Lys Arg Phe Pro Gln Leu Lys Gly Lys Ile
        275                 280                 285

Ala Pro Ala Asp Asn Ser Glu Leu Pro Gln Gly Gly Arg Val His Asn
    290                 295                 300

Glu Lys Thr Lys Ala Leu Leu Gly Tyr Ile Phe Lys Asp Leu Glu Glu
305                 310                 315                 320

Ile Val Val Asp Met Ala Asp Gln Ile Leu Lys Val Gln Glu Gln
                325                 330                 335

<210> SEQ ID NO 2
<211> LENGTH: 1008
<212> TYPE: DNA
<213> ORGANISM: Vanderwaltozyma polyspora

<400> SEQUENCE: 2
atgagtgttt tagttacagg tgctactggt tacattgcat tacatgtaat tgacctttg      60 ttaaaggaaa attacagagt aattggtact gttagatcaa aggaaaaggc tgctaagtta    120
gagaaacaat ttaattataa taaggattta acttttgaaa ttgttgaaga tattgctaat    180
ttatctgctt ttgatcatgt aattaaaaat catgctaatg aaattaacta tgtgattcat    240
atggcttcac ctgttacttt tactgcagat gattttgaaa aagatatctt aatcccagct    300
gttaatggta ctaaaggtat ccttgaatca attaagcaat atgctccaaa atctgtgaag    360
aaatttgtta taacttcttc aattgctgcc atgatggatt taacaaatcc aactgcaatt    420 taacagaac aatcatggaa cccaactact tgggagcaag ctcaggaaaa tgggattgct    480
gcatattcag gttcaaagaa atttgcagaa aaagctgctt ggaacttctt agaagagaat    540
aaaggtattt tgattttaa attaactacg atcaacccag tttttgtctt tggtcctcag    600
aaatttgatg aagacgccaa gggtaaactg aattcctcat gtgaaatcat caaggaagct    660
atgtttgctc caacagaaag tgaaattgat aaatctgttt ttggtagtta tgttgatgta    720
cgtgatgtag caagagctca tgtctgttct ttacataatg atgagttaac tggtaaaagg    780
ttgatcttgt caaatgcttc attcactaag caaaatattg tcaatattat gaacaagcgt    840
ttccctcaat tgaagggcaa gattgcacct gcagataata gcgagttacc tcaaggaggt    900
cgtgtccata acgagaagac taaggctcta ttgggttata ttttaagga tttagaagaa    960 attgttgtcg atatggctga tcaaatattg aaggttcaag aacaatag            1008

<210> SEQ ID NO 3
<211> LENGTH: 1008
<212> TYPE: DNA
<213> ORGANISM: Artificial Sequence
<220> FEATURE:

<223> OTHER INFORMATION: Mutational gene sequence for cutting NdeI site

<400> SEQUENCE: 3

| | | | | | |
|---|---|---|---|---|---|
| atgagtgttt | tagttacagg | tgctactggt | tacattgcat | tacatgtaat | tgaccttttg | 60
| ttaaaggaaa | attacagagt | aattggtact | gttagatcaa | aggaaaaggc | tgctaagtta | 120
| gagaaacaat | ttaattataa | taaggattta | acttttgaaa | ttgttgaaga | tattgctaat | 180
| ttatctgctt | ttgatcatgt | aattaaaaat | catgctaatg | aaattaacta | tgtgattcac | 240
| atggcttcac | ctgttacttt | tactgcagat | gattttgaaa | aagatatctt | aatcccagct | 300
| gttaatggta | ctaaaggtat | ccttgaatca | attaagcaat | atgctccaaa | atctgtgaag | 360
| aaatttgtta | taacttcttc | aattgctgcc | atgatggatt | taacaaatcc | aactgcaatt | 420
| ttaacagaac | aatcatggaa | cccaactact | tgggagcaag | ctcaggaaaa | tgggattgct | 480
| gcatattcag | gttcaaagaa | atttgcagaa | aaagctgctt | ggaacttctt | agaagagaat | 540
| aaaggtattg | ttgattttaa | attaactacg | atcaacccag | tttttgtctt | tggtcctcag | 600
| aaatttgatg | aagacgccaa | gggtaaactg | aattcctcat | gtgaaatcat | caaggaagct | 660
| atgtttgctc | caacagaaag | tgaaattgat | aaatctgttt | ttggtagtta | tgttgatgta | 720
| cgtgatgtag | caagagctca | tgtctgttct | ttacataatg | atgagttaac | tggtaaaagg | 780
| ttgatcttgt | caaatgcttc | attcactaag | caaaatattg | tcaatattat | gaacaagcgt | 840
| ttccctcaat | tgaagggcaa | gattgcacct | gcagataata | gcgagttacc | tcaaggaggt | 900
| cgtgtcccata | acgagaagac | taaggctcta | ttgggttata | ttttaaga | tttagaagaa | 960
| attgttgtcg | atatggctga | tcaaatattg | aaggttcaag | aacaatag | | 1008

<210> SEQ ID NO 4
<211> LENGTH: 31
<212> TYPE: DNA
<213> ORGANISM: Artificial Sequence
<220> FEATURE:
<223> OTHER INFORMATION: Primer for PCR to amplify a wild type gene

<400> SEQUENCE: 4
gggaattcca tatgagtgtt ttagttacag g                                 31

<210> SEQ ID NO 5
<211> LENGTH: 35
<212> TYPE: DNA
<213> ORGANISM: Artificial Sequence
<220> FEATURE:
<223> OTHER INFORMATION: Primer for PCR to amplify a wild type gene

<400> SEQUENCE: 5
atacgcgtcg acttactatt gttcttgaac cttca                             35

<210> SEQ ID NO 6
<211> LENGTH: 33
<212> TYPE: DNA
<213> ORGANISM: Artificial Sequence
<220> FEATURE:
<223> OTHER INFORMATION: Primer for PCR to amplify a mutation type gene

<400> SEQUENCE: 6
gttaatttca ttagcgcgat ttttaattac atg                               33

<210> SEQ ID NO 7
<211> LENGTH: 33
<212> TYPE: DNA
<213> ORGANISM: Artificial Sequence -continued

```
<220> FEATURE:
<223> OTHER INFORMATION: Primer for PCR to amplify a mutation type gene

<400> SEQUENCE: 7
catgtaatta aaaatcgcgc taatgaaatt aac                                   33

<210> SEQ ID NO 8
<211> LENGTH: 33
<212> TYPE: DNA
<213> ORGANISM: Artificial Sequence
<220> FEATURE:
<223> OTHER INFORMATION: Primer for PCR to amplify a mutation type gene

<400> SEQUENCE: 8
gatcaacctt tcaccgctta actcatcatt atg                                   33

<210> SEQ ID NO 9
<211> LENGTH: 33
<212> TYPE: DNA
<213> ORGANISM: Artificial Sequence
<220> FEATURE:
<223> OTHER INFORMATION: Primer for PCR to amplify a mutation type gene

<400> SEQUENCE: 9
cataatgatg agttaagcgg tgaaaggttg atc                                   33

<210> SEQ ID NO 10
<211> LENGTH: 33
<212> TYPE: DNA
<213> ORGANISM: Artificial Sequence
<220> FEATURE:
<223> OTHER INFORMATION: Primer for PCR to amplify a mutation type gene

<400> SEQUENCE: 10
ctcgttatgg acacgatctc cttgaggtaa ctc                                   33

<210> SEQ ID NO 11
<211> LENGTH: 33
<212> TYPE: DNA
<213> ORGANISM: Artificial Sequence
<220> FEATURE:
<223> OTHER INFORMATION: Primer for PCR to amplify a mutation type gene

<400> SEQUENCE: 11
gagttacctc aaggagatcg tgtccataac gag                                   33

<210> SEQ ID NO 12
<211> LENGTH: 33
<212> TYPE: DNA
<213> ORGANISM: Artificial Sequence
<220> FEATURE:
<223> OTHER INFORMATION: Primer for PCR to amplify a mutation type gene

<400> SEQUENCE: 12
gttaatttca ttagcgcgat ttttaattac atg                                   33

<210> SEQ ID NO 13
<211> LENGTH: 33
<212> TYPE: DNA
<213> ORGANISM: Artificial Sequence
<220> FEATURE:
<223> OTHER INFORMATION: Primer for PCR to amplify a mutation type gene

<400> SEQUENCE: 13
catgtaatta aaaatcgcgc taatgaaatt aac                                   33
```

<210> SEQ ID NO 14
<211> LENGTH: 35
<212> TYPE: DNA
<213> ORGANISM: Artificial Sequence
<220> FEATURE:
<223> OTHER INFORMATION: Primer for PCR to amplify a mutation type gene

<400> SEQUENCE: 14 ggatacctttt agtaccaata acagctggga ttaag                         35

<210> SEQ ID NO 15
<211> LENGTH: 35
<212> TYPE: DNA
<213> ORGANISM: Artificial Sequence
<220> FEATURE:
<223> OTHER INFORMATION: Primer for PCR to amplify a mutation type gene

<400> SEQUENCE: 15
cttaatccca gctgttattg gtactaaagg tatcc                          35

<210> SEQ ID NO 16
<211> LENGTH: 36
<212> TYPE: DNA
<213> ORGANISM: Artificial Sequence
<220> FEATURE:
<223> OTHER INFORMATION: Primer for PCR to amplify a mutation type gene

<400> SEQUENCE: 16
tttatcaatt tcactgcctg ttggagcaaa catagc                         36

<210> SEQ ID NO 17
<211> LENGTH: 36
<212> TYPE: DNA
<213> ORGANISM: Artificial Sequence
<220> FEATURE:
<223> OTHER INFORMATION: Primer for PCR to amplify a mutation type gene

<400> SEQUENCE: 17
gctatgtttg ctccaacagg cagtgaaatt gataaa                         36

<210> SEQ ID NO 18
<211> LENGTH: 33
<212> TYPE: DNA
<213> ORGANISM: Artificial Sequence
<220> FEATURE:
<223> OTHER INFORMATION: Primer for PCR to amplify a mutation type gene

<400> SEQUENCE: 18
gatcaacctt ttaccgctta actcatcatt atg                            33

<210> SEQ ID NO 19
<211> LENGTH: 33
<212> TYPE: DNA
<213> ORGANISM: Artificial Sequence
<220> FEATURE:
<223> OTHER INFORMATION: Primer for PCR to amplify a mutation type gene

<400> SEQUENCE: 19
cataatgatg agttaagcgg taaaaggttg atc                            33

<210> SEQ ID NO 20
<211> LENGTH: 32
<212> TYPE: DNA
<213> ORGANISM: Artificial Sequence
<220> FEATURE:
<223> OTHER INFORMATION: Primer for PCR to amplify a mutation type gene

<400> SEQUENCE: 20
gacaagatca acctttcacc agttaactca tc                                         32

<210> SEQ ID NO 21
<211> LENGTH: 32
<212> TYPE: DNA
<213> ORGANISM: Artificial Sequence
<220> FEATURE:
<223> OTHER INFORMATION: Primer for PCR to amplify a mutation type gene

<400> SEQUENCE: 21
gatgagttaa ctggtgaaag gttgatcttg tc                                         32

<210> SEQ ID NO 22
<211> LENGTH: 29
<212> TYPE: DNA
<213> ORGANISM: Artificial Sequence
<220> FEATURE:
<223> OTHER INFORMATION: Primer for PCR to amplify a mutation type gene

<400> SEQUENCE: 22
tttgcatagt gaacggagca tttgacaag                                             29

<210> SEQ ID NO 23
<211> LENGTH: 29
<212> TYPE: DNA
<213> ORGANISM: Artificial Sequence
<220> FEATURE:
<223> OTHER INFORMATION: Primer for PCR to amplify a mutation type gene

<400> SEQUENCE: 23
cttgtcaaat gctccgttca ctatgcaaa                                             29

<210> SEQ ID NO 24
<211> LENGTH: 33
<212> TYPE: DNA
<213> ORGANISM: Artificial Sequence
<220> FEATURE:
<223> OTHER INFORMATION: Primer for PCR to amplify a mutation type gene

<400> SEQUENCE: 24
ctcgttatgg acacgatctc cttgaggtaa ctc                                        33

<210> SEQ ID NO 25
<211> LENGTH: 33
<212> TYPE: DNA
<213> ORGANISM: Artificial Sequence
<220> FEATURE:
<223> OTHER INFORMATION: Primer for PCR to amplify a mutation type gene

<400> SEQUENCE: 25
gagttacctc aaggagatcg tgtccataac gag                                        33

<210> SEQ ID NO 26
<211> LENGTH: 29
<212> TYPE: DNA
<213> ORGANISM: Artificial Sequence
<220> FEATURE:
<223> OTHER INFORMATION: Primer for PCR to amplify a mutation type gene

<400> SEQUENCE: 26
ccagtagcac ctgtaactaa aacaatcat                                             29

<210> SEQ ID NO 27

```
<211> LENGTH: 29
<212> TYPE: DNA
<213> ORGANISM: Artificial Sequence
<220> FEATURE:
<223> OTHER INFORMATION: Primer for PCR to amplify a mutation type gene

<400> SEQUENCE: 27
atgattgttt tagttacagg tgctactgg                                        29

<210> SEQ ID NO 28
<211> LENGTH: 36
<212> TYPE: DNA
<213> ORGANISM: Artificial Sequence
<220> FEATURE:
<223> OTHER INFORMATION: Primer for PCR to amplify a mutation type gene

<400> SEQUENCE: 28
ggcagcaatt gaagaagtca gaacaaattt cttcac                                36

<210> SEQ ID NO 29
<211> LENGTH: 36
<212> TYPE: DNA
<213> ORGANISM: Artificial Sequence
<220> FEATURE:
<223> OTHER INFORMATION: Primer for PCR to amplify a mutation type gene

<400> SEQUENCE: 29
gtgaagaaat ttgttctgac ttcttcaatt gctgcc                                36

<210> SEQ ID NO 30
<211> LENGTH: 32
<212> TYPE: DNA
<213> ORGANISM: Artificial Sequence
<220> FEATURE:
<223> OTHER INFORMATION: Primer for PCR to amplify a mutation type gene

<400> SEQUENCE: 30
cctttattct cttcaaagaa gttccaagca gc                                    32

<210> SEQ ID NO 31
<211> LENGTH: 32
<212> TYPE: DNA
<213> ORGANISM: Artificial Sequence
<220> FEATURE:
<223> OTHER INFORMATION: Primer for PCR to amplify a mutation type gene

<400> SEQUENCE: 31
gctgcttgga acttctttga agagaataaa gg                                    32

<210> SEQ ID NO 32
<211> LENGTH: 28
<212> TYPE: DNA
<213> ORGANISM: Artificial Sequence
<220> FEATURE:
<223> OTHER INFORMATION: Primer for PCR to amplify a mutation type gene

<400> SEQUENCE: 32
ggaccaaaga ccagaactgg gttgatcg                                         28

<210> SEQ ID NO 33
<211> LENGTH: 28
<212> TYPE: DNA
<213> ORGANISM: Artificial Sequence
<220> FEATURE:
<223> OTHER INFORMATION: Primer for PCR to amplify a mutation type gene

<400> SEQUENCE: 33
```
cgatcaaccc agttctggtc tttggtcc                                     28

<210> SEQ ID NO 34
<211> LENGTH: 34
<212> TYPE: DNA
<213> ORGANISM: Artificial Sequence
<220> FEATURE:
<223> OTHER INFORMATION: Primer for PCR to amplify a mutation type gene

<400> SEQUENCE: 34
ctgttggagc aaacatcact tccttgatga tttc                              34

<210> SEQ ID NO 35
<211> LENGTH: 34
<212> TYPE: DNA
<213> ORGANISM: Artificial Sequence
<220> FEATURE:
<223> OTHER INFORMATION: Primer for PCR to amplify a mutation type gene

<400> SEQUENCE: 35
gaaatcatca aggaagtgat gtttgctcca acag                              34

<210> SEQ ID NO 36
<211> LENGTH: 35
<212> TYPE: DNA
<213> ORGANISM: Artificial Sequence
<220> FEATURE:
<223> OTHER INFORMATION: Primer for PCR to amplify a mutation type gene

<400> SEQUENCE: 36
cgtacatcaa catagttacc aaaaacagat ttatc                             35

<210> SEQ ID NO 37
<211> LENGTH: 35
<212> TYPE: DNA
<213> ORGANISM: Artificial Sequence
<220> FEATURE:
<223> OTHER INFORMATION: Primer for PCR to amplify a mutation type gene

<400> SEQUENCE: 37
gataaatctg ttttttggtaa ctatgttgat gtacg                            35

<210> SEQ ID NO 38
<211> LENGTH: 35
<212> TYPE: DNA
<213> ORGANISM: Artificial Sequence
<220> FEATURE:
<223> OTHER INFORMATION: Primer for PCR to amplify a mutation type gene

<400> SEQUENCE: 38
gctacatcac gtacatcaat ataactacca aaaac                             35

<210> SEQ ID NO 39
<211> LENGTH: 35
<212> TYPE: DNA
<213> ORGANISM: Artificial Sequence
<220> FEATURE:
<223> OTHER INFORMATION: Primer for PCR to amplify a mutation type gene

<400> SEQUENCE: 39
gtttttggta gttatattga tgtacgtgat gtagc                             35

<210> SEQ ID NO 40
<211> LENGTH: 33
<212> TYPE: DNA

```
<213> ORGANISM: Artificial Sequence
<220> FEATURE:
<223> OTHER INFORMATION: Primer for PCR to amplify a mutation type gene

<400> SEQUENCE: 40
gatcaacctt ttaccgctta actcatcatt atg                           33

<210> SEQ ID NO 41
<211> LENGTH: 33
<212> TYPE: DNA
<213> ORGANISM: Artificial Sequence
<220> FEATURE:
<223> OTHER INFORMATION: Primer for PCR to amplify a mutation type gene

<400> SEQUENCE: 41
cataatgatg agttaagcgg taaaaggttg atc                           33

<210> SEQ ID NO 42
<211> LENGTH: 40
<212> TYPE: DNA
<213> ORGANISM: Artificial Sequence
<220> FEATURE:
<223> OTHER INFORMATION: Primer for PCR to amplify a mutation type gene

<400> SEQUENCE: 42
gcatagtgaa tgaagctttt gacaagatca acctttcacc                    40

<210> SEQ ID NO 43
<211> LENGTH: 40
<212> TYPE: DNA
<213> ORGANISM: Artificial Sequence
<220> FEATURE:
<223> OTHER INFORMATION: Primer for PCR to amplify a mutation type gene

<400> SEQUENCE: 43
ggtgaaaggt tgatcttgtc aaaagcttca ttcactatgc                    40

<210> SEQ ID NO 44
<211> LENGTH: 33
<212> TYPE: DNA
<213> ORGANISM: Artificial Sequence
<220> FEATURE:
<223> OTHER INFORMATION: Primer for PCR to amplify a mutation type gene

<400> SEQUENCE: 44
ctcgttatgg acacgatctc cttgaggtaa ctc                           33

<210> SEQ ID NO 45
<211> LENGTH: 33
<212> TYPE: DNA
<213> ORGANISM: Artificial Sequence
<220> FEATURE:
<223> OTHER INFORMATION: Primer for PCR to amplify a mutation type gene

<400> SEQUENCE: 45
gagttacctc aaggagatcg tgtccataac gag                           33

<210> SEQ ID NO 46
<211> LENGTH: 37
<212> TYPE: DNA
<213> ORGANISM: Artificial Sequence
<220> FEATURE:
<223> OTHER INFORMATION: Primer for PCR to amplify a mutation type gene

<400> SEQUENCE: 46
cttctcgtta tggacgcaac ctccttgagg taactcg                       37
```

```
<210> SEQ ID NO 47
<211> LENGTH: 37
<212> TYPE: DNA
<213> ORGANISM: Artificial Sequence
<220> FEATURE:
<223> OTHER INFORMATION: Primer for PCR to amplify a mutation type gene

<400> SEQUENCE: 47
cgagttacct caaggaggtt gcgtccataa cgagaag                              37
```

MODIFIED CARBONYL REDUCING ENZYME AND GENE

TECHNICAL FIELD

The present invention relates to altered carbonyl reductases, genes thereof, vectors containing such genes, and transformants obtained by transformation with such vectors.

BACKGROUND ART

A method of asymmetrically reducing the carbonyl group of a carbonyl compound using a microorganism or an enzyme is known as one of the methods for producing optically active alcohols useful as starting materials or intermediates for the synthesis of pharmaceuticals or agricultural chemicals. Asymmetric enzymes reducing carbonyl compounds (hereinafter, carbonyl reductases) are useful in the production of various optically active alcohols.

The asymmetric reduction reactions using carbonyl reductases may suffer from deactivation of the enzyme or inhibition of the enzymatic reaction due to the presence of the substrate or generated products, the acid or alkali used in pH adjustment, the surfactant or organic solvent added to improve the properties of the reaction mixture, or the like. Accordingly, carbonyl reductases capable of avoiding the deactivation of the enzyme or inhibition of the enzyme reaction by the organic solvent or the like provide shortening of the reaction time and improvement in the reaction yield, and are thus more useful in the industrial production of optically active alcohols.

For example, there have been attempts to acquire organic solvent resistance by random mutation, and Patent Literature 1 and Non Patent Literature 1 describe reductases that are resistant to 2-propanol or dimethyl sulfoxide.

However, there are only a few enzymes resistant to dimethylformamide, an industrially highly useful organic solvent, and at present no reductase having practical levels of dimethylformamide resistance has been reported.

CITATION LIST

Patent Literature

Patent Literature 1: JP 2009-225773 A

Non Patent Literature

Non Patent Literature 1: Chem Sus Chem, 1, 431-436 (2008)

SUMMARY OF INVENTION

Technical Problem

Many of pharmaceutical intermediates such as ezetimibe and montelukast have higher solubility in dimethylformamide than in 2-propanol and dimethyl sulfoxide. If a dimethylformamide-resistant enzyme can be used in the production of such a compound, the properties of the reaction mixture can be improved, and thus higher productivity can be expected than in the case of using other organic solvents.

An object of the present invention is therefore to modify a wild-type enzyme that is less reactive in the presence of dimethylformamide to provide altered carbonyl reductases having better reactivity in the presence of the organic solvent than the wild-type enzyme, and/or to provide transformants producing such reductases.

Solution to Problem

The present inventors have found altered carbonyl reductases having better reactivity in the presence of an organic solvent than the wild-type enzyme, from among a mutant enzyme library prepared by randomly mutating the wild-type enzyme gene, thereby arriving at completion of the present invention.

Specifically, the present invention relates to a polypeptide having the following properties (a) to (c):

(a) the polypeptide has an amino acid sequence having at least 78% sequence identity to the amino acid sequence of SEQ ID NO:1 in the sequence listing;

(b) the polypeptide reduces 2-pentanone into 2-pentanol; and (c) the polypeptide has higher reactivity to a carbonyl compound in the presence of an organic solvent and/or higher thermal stability than a carbonyl reductase having the amino acid sequence of SEQ ID NO:1 in the sequence listing.

Preferably, the organic solvent is dimethylformamide.

Preferably, the polypeptide contains an amino acid substitution, relative to the amino acid sequence of SEQ ID NO:1 in the sequence listing, at one or more positions selected from the group consisting of positions 2, 22, 25, 39, 42, 45, 51, 56, 71, 87, 90, 102, 109, 124, 135, 138, 155, 159, 175, 177, 183, 190, 195, 212, 220, 226, 228, 236, 238, 250, 254, 257, 259, 265, 267, 270, 279, 298, 300, 301, and 331.

Preferably, the amino acid substitution is one or more of the following amino acid substitutions relative to the amino acid sequence of SEQ ID NO:1 in the sequence listing:

substitutions at position 2 with isoleucine, at position 22 with arginine, at position 25 with phenylalanine, at position 39 with arginine, at position 42 with arginine, at position 45 with aspartic acid, at position 51 with alanine, at position 56 with lysine, at position 71 with asparagine or arginine, at position 87 with isoleucine, at position 90 with glycine, at position 102 with isoleucine, at position 109 with glycine, at position 124 with leucine, at position 135 with alanine, at position 138 with asparagine, at position 155 with leucine or arginine, at position 159 with phenylalanine, at position 175 with aspartic acid, at position 177 with phenylalanine, at position 183 with threonine, at position 190 with serine, at position 195 with leucine, at position 212 with phenylalanine, threonine, or tyrosine, at position 220 with valine, at position 226 with glycine, at position 228 with valine, at position 236 with asparagine, at position 238 with isoleucine, at position 250 with proline, at position 254 with asparagine, at position 257 with serine, at position 259 with glutamic acid, at position 265 with lysine, at position 267 with proline, at position 270 with methionine, at position 279 with arginine, at position 298 with proline, at position 300 with aspartic acid, at position 301 with cysteine, and at position 331 with phenylalanine.

Preferably, the amino acid substitution is one or more of the following amino acid substitutions relative to the amino acid sequence of SEQ ID NO:1 in the sequence listing:

substitutions at position 2 with isoleucine, at position 45 with aspartic acid, at position 71 with asparagine or arginine, at position 102 with isoleucine, at position 124 with leucine, at position 175 with aspartic acid, at position 177 with phenylalanine, at position 183 with threonine, at position 195 with leucine, at position 220 with valine, at position 226 with glycine, at position 236 with asparagine, at position 238 with isoleucine, at position 257 with serine, at position 259 with glutamic acid, at position 265 with lysine, at position 267 with proline, at position 270 with methionine, at position 300 with aspartic acid, and at position 301 with cysteine, and the polypeptide has better stability to the organic solvent than the carbonyl reductase having the amino acid sequence of SEQ ID NO:1 in the sequence listing.

Preferably, the amino acid substitution is selected from the following amino acid substitutions (1) to (35) relative to the amino acid sequence of SEQ ID NO:1 in the sequence listing:

(1) an amino acid substitution at position 71 with asparagine and at position 195 with leucine;

(2) an amino acid substitution at position 71 with arginine and at position 259 with glutamic acid;

(3) an amino acid substitution at position 71 with arginine and at position 270 with methionine;

(4) an amino acid substitution at position 71 with arginine and at position 300 with aspartic acid;

(5) an amino acid substitution at position 102 with isoleucine and at position 270 with methionine;

(6) an amino acid substitution at position 177 with phenylalanine and at position 220 with valine;

(7) an amino acid substitution at position 226 with glycine and at position 270 with methionine;

(8) an amino acid substitution at position 257 with serine and at position 259 with glutamic acid;

(9) an amino acid substitution at position 257 with serine and at position 270 with methionine;

(10) an amino acid substitution at position 259 with glutamic acid and at position 270 with methionine;

(11) an amino acid substitution at position 259 with glutamic acid and at position 300 with aspartic acid;

(12) an amino acid substitution at position 267 with proline and at position 270 with methionine;

(13) an amino acid substitution at position 270 with methionine and at position 300 with aspartic acid;

(14) an amino acid substitution at position 2 with isoleucine, at position 259 with glutamic acid, and at position 270 with methionine;

(15) an amino acid substitution at position 45 with aspartic acid, at position 175 with aspartic acid, and at position 183 with threonine;

(16) an amino acid substitution at position 102 with isoleucine, at position 226 with glycine, and at position 267 with proline;

(17) an amino acid substitution at position 124 with leucine, at position 259 with glutamic acid, and at position 270 with methionine;

(18) an amino acid substitution at position 177 with phenylalanine, at position 259 with glutamic acid, and at position 270 with methionine;

(19) an amino acid substitution at position 220 with valine, at position 259 with glutamic acid, and at position 270 with methionine;

(20) an amino acid substitution at position 236 with asparagine, at position 259 with glutamic acid, and at position 270 with methionine;

(21) an amino acid substitution at position 238 with isoleucine, at position 259 with glutamic acid, and at position 270 with methionine;

(22) an amino acid substitution at position 257 with serine, at position 259 with glutamic acid, and at position 270 with methionine;

(23) an amino acid substitution at position 257 with serine, at position 259 with glutamic acid, and at position 300 with aspartic acid;

(24) an amino acid substitution at position 259 with glutamic acid, at position 265 with lysine, and at position 270 with methionine;

(25) an amino acid substitution at position 259 with glutamic acid, at position 270 with methionine, and at position 300 with aspartic acid;

(26) an amino acid substitution at position 259 with glutamic acid, at position 270 with methionine, and at position 301 with cysteine;

(27) an amino acid substitution at position 2 with isoleucine and at position 238 with isoleucine;

(28) an amino acid substitution at position 71 with asparagine and at position 195 with leucine;

(29) an amino acid substitution at position 109 with glycine and at position 331 with phenylalanine;

(30) an amino acid substitution at position 124 with leucine and at position 236 with asparagine;

(31) an amino acid substitution at position 159 with phenylalanine and at position 259 with glutamic acid;

(32) an amino acid substitution at position 42 with arginine, at position 155 with arginine, and at position 279 with arginine;

(33) an amino acid substitution at position 45 with aspartic acid, at position 175 with aspartic acid, and at position 183 with threonine;

(34) an amino acid substitution at position 155 with leucine, at position 250 with proline, and at position 298 with proline; and

(35) an amino acid substitution at position 56 with lysine, at position 138 with asparagine, at position 190 with serine, and at position 254 with asparagine.

Preferably, the amino acid substitution is one or more of the following amino acid substitutions:

substitutions at position 22 with arginine, at position 39 with arginine, at position 51 with alanine, at position 87 with isoleucine, at position 90 with glycine, at position 259 with glutamic acid, and at position 270 with methionine, and the polypeptide has better resistance to reaction inhibition by the organic solvent than the carbonyl reductase having the amino acid sequence of SEQ ID NO:1 in the sequence listing.

Preferably, the amino acid substitution is one or more of the following amino acid substitutions (1) to (7) relative to the amino acid sequence of SEQ ID NO:1 in the sequence listing:

(1) an amino acid substitution at position 22 with arginine;

(2) an amino acid substitution at position 22 with arginine and at position 87 with isoleucine;

(3) an amino acid substitution at position 39 with arginine;

(4) an amino acid substitution at position 39 with arginine and at position 51 with alanine;

(5) an amino acid substitution at position 51 with alanine;

(6) an amino acid substitution at position 87 with isoleucine; and (7) an amino acid substitution at position 90 with glycine.

The present invention also relates to a polynucleotide encoding the polypeptide.

The present invention also relates to a vector containing the polynucleotide.

Preferably, the vector further contains a polynucleotide that encodes a polypeptide capable of regenerating a reduced coenzyme.

Preferably, the polypeptide capable of regenerating a reduced coenzyme is glucose dehydrogenase.

The present invention also relates to a transformant obtained by transformation of a host cell with the vector.

Preferably, the host cell is *Escherichia coli*.

The present invention also relates to a method for producing an alcohol compound, including allowing the polypeptide, or the transformant and/or a treated product thereof to act on a carbonyl compound.

Preferably, the carbonyl compound is an unsymmetrical ketone, and the alcohol compound is an optically active alcohol.

Preferably, the carbonyl compound is an unsymmetrical ketone represented by the following formula (1):

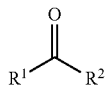

(1)

wherein $R^1$ and $R^2$ are each a hydrogen atom, a halogen atom, an optionally substituted alkyl group, an optionally substituted aralkyl group, an optionally substituted aryl group, an optionally substituted alkoxy group, an amino group, or a nitro group, or $R^1$ and $R^2$ may be joined together to form a ring, provided that $R^1$ and $R^2$ have different structures, and the alcohol compound is an optically active alcohol represented by the following formula (2):

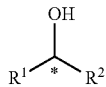

(2)

wherein $R^1$ and $R^2$ are the same as described above, and * represents an asymmetric carbon atom.

Advantageous Effects of Invention

The present invention provides altered carbonyl reductases having better reactivity in the presence of an organic solvent than the wild-type enzyme, genes thereof, vectors containing such genes, transformants obtained by transformation with such vectors, and methods for producing treated products of such transformants.

DESCRIPTION OF EMBODIMENTS

The polypeptide of the present invention characteristically has the following properties (a) to (c):

(a) the polypeptide has an amino acid sequence having at least 78% sequence identity to the amino acid sequence of SEQ ID NO:1 in the sequence listing;

(b) the polypeptide reduces 2-pentanone into 2-pentanol; and (c) the polypeptide has higher reactivity to a carbonyl compound in the presence of an organic solvent and/or higher thermal stability than a carbonyl reductase having the amino acid sequence of SEQ ID NO:1 in the sequence listing.

[Nomenclature for Description of Mutations]

In the present specification, amino acids, peptides, and proteins are represented using abbreviations, as indicated below, approved by the IUPAC-IUB Commission on Biochemical Nomenclature (CBN). Further, the left and right ends of an amino acid sequence of a peptide or protein are, respectively, the N- and C-termini unless otherwise specified. For ease of reference, the following commonly used nomenclatures are adapted. One is the following nomenclature: "original amino acid; position; substituted amino acid". For example, the substitution of tyrosine at position 64 with aspartic acid is designated as "Y64D". Multiple mutations are separated by hyphens "-". For example, "S41A-Y64D" represents mutations at positions 41 and 64 substituting serine with alanine and tyrosine with aspartic acid, respectively.

ABBREVIATIONS FOR AMINO ACIDS

A=Ala=alanine, C=Cys=cysteine,
D=Asp=aspartic acid, E=Glu=glutamic acid,
F=Phe=phenylalanine, G=Gly=glycine,
H=His=histidine, I=Ile=isoleucine,
K=Lys=lysine, L=Leu=leucine,
M=Met=methionine, N=Asn=asparagine,
P=Pro=proline, Q=Gln=glutamine,
R=Arg=arginine, S=Ser=serine,
T=Thr=threonine, V=Val=valine,
W=Trp=tryptophan, Y=Tyr=tyrosine
[Sequence Identity]

The "sequence identity" for polypeptides and polynucleotides refers to the value obtained by optimally aligning two polypeptides or polynucleotides to be compared, counting the number of positions of amino acids or nucleic acid bases (e.g., A, T, C, G, U or I) matched between both sequences, dividing the counted number by the total number of the compared bases, and multiplying the result of the division by 100.

The sequence identity can be calculated, for example, using the following sequence analysis tools: GCG Wisconsin Package (University of Wisconsin), the ExPASy World Wide Web molecular biology server (Swiss Institute of Bioinformatics), BLAST (U.S. National Center for Biotechnology Information), and GENETYX (GENETYX Corporation).

In the present invention, the wild-type enzyme before mutation is a polypeptide that has 335 amino acid residues represented by SEQ ID NO:1 in the sequence listing and is capable of reducing 2-pentanone into 2-pentanol.

Although the source of the polypeptide is not limited, the polypeptide is preferably a carbonyl reductase derived from a microorganism belonging to the family Saccharomycetaceae, more preferably the genus *Vanderwaltozyma*, still more preferably a microorganism belonging to the species *Vanderwaltozyma polyspora*, and particularly preferably from *Vanderwaltozyma polyspora* NBRC 0996. The microorganisms are available from the Incorporated Administrative Agency, National Institute of Technology and Evaluation, Department of Biotechnology, Biological Resource Center (NBRC: 2-5-8 Kazusakamatari, Kisarazu-shi, Chiba, 292-0818 JAPAN).

The wild-type enzyme in the present invention is encoded by the polynucleotide of SEQ ID NO:2 in the sequence listing. For example, the wild-type enzyme gene can be obtained from microorganisms belonging to the family Saccharomycetaceae, preferably the genus *Vanderwaltozyma*, more preferably the species *Vanderwaltozyma polyspora*, and still more preferably *Vanderwaltozyma polyspora* NBRC 0996 using common genetic engineering techniques described in, for example, Molecular Cloning 2nd Edition (Joseph Sambrook, Cold Spring Harbor Laboratory Press (1989)).

Specifically, the wild-type enzyme gene can be prepared by performing PCR using the genomic DNA of *Vanderwaltozyma polyspora* NBRC 0996 as described in [Reference Example 1] to amplify a polynucleotide encoding the amino acid sequence of SEQ ID NO:1 or the polynucleotide of SEQ ID NO:2.

The polypeptide of the present invention may be obtained by altering the amino acid sequence of SEQ ID NO: 1.

Examples of alterations of the amino acid sequence of SEQ ID NO:1 include substitutions, additions, insertions, and deletions. The sequence may include only one type of alteration (e.g. substitution) or two or more types of alterations (e.g. substitution and insertion). The term "amino acids" means, for example, 40, preferably 20, more preferably 10, and still more preferably 8, 5, 4, 3, or 2 amino acids.

Moreover, the sequence identity between the altered amino acid sequence and the amino acid sequence of SEQ ID NO:1 is at least 85%, preferably at least 90%, more preferably at least 92%, still more preferably at least 95%, at least 97%, at least 98%, at least 98.5%, or at least 99%.

Although a substitution, insertion, deletion, or addition of an amino acid may be introduced at any position in the amino acid sequence of SEQ ID NO:1 in the sequence listing, the polypeptide preferably contains an amino acid substitutions, relative to the amino acid sequence of SEQ ID NO:1 in the sequence listing, at one or more positions selected from positions 2, 22, 25, 39, 42, 45, 51, 56, 71, 87, 90, 102, 109, 124, 135, 138, 155, 159, 175, 177, 183, 190, 195, 212, 220, 226, 228, 236, 238, 250, 254, 257, 259, 265, 267, 270, 279, 298, 300, 301, and 331.

More preferably, the polypeptide contains one or more of the following amino acid substitutions relative to the amino acid sequence of SEQ ID NO:1 in the sequence listing:

substitutions at position 2 with isoleucine, at position 22 with arginine, at position 25 with phenylalanine, at position 39 with arginine, at position 42 with arginine, at position 45 with aspartic acid, at position 51 with alanine, at position 56 with lysine, at position 71 with asparagine or arginine, at position 87 with isoleucine, at position 90 with glycine, at position 102 with isoleucine, at position 109 with glycine, at position 124 with leucine, at position 135 with alanine, at position 138 with asparagine, at position 155 with leucine or arginine, at position 159 with phenylalanine, at position 175 with aspartic acid, at position 177 with phenylalanine, at position 183 with threonine, at position 190 with serine, at position 195 with leucine, at position 212 with phenylalanine, threonine, or tyrosine, at position 220 with valine, at position 226 with glycine, at position 228 with valine, at position 236 with asparagine, at position 238 with isoleucine, at position 250 with proline, at position 254 with asparagine, at position 257 with serine, at position 259 with glutamic acid, at position 265 with lysine, at position 267 with proline, at position 270 with methionine, at position 279 with arginine, at position 298 with proline, at position 300 with aspartic acid, at position 301 with cysteine, and at position 331 with phenylalanine.

Moreover, from the standpoint of enhancing the stability to an organic solvent, the polypeptide of the present invention preferably contains one or more of the following amino acid substitutions relative to the amino acid sequence of SEQ ID NO:1 in the sequence listing:

substitutions at position 2 with isoleucine, at position 45 with aspartic acid, at position 71 with asparagine or arginine, at position 102 with isoleucine, at position 124 with leucine, at position 175 with aspartic acid, at position 177 with phenylalanine, at position 183 with threonine, at position 195 with leucine, at position 220 with valine, at position 226 with glycine, at position 236 with asparagine, at position 238 with isoleucine, at position 257 with serine, at position 259 with glutamic acid, at position 265 with lysine, at position 267 with proline, at position 270 with methionine, at position 300 with aspartic acid, and at position 301 with cysteine.

Further, the polypeptide of the present invention more preferably contains an amino acid substitution selected from the following amino acid substitutions (1) to (35) relative to the amino acid sequence of SEQ ID NO:1 in the sequence listing:

(1) an amino acid substitution at position 71 with asparagine and at position 195 with leucine;

(2) an amino acid substitution at position 71 with arginine and at position 259 with glutamic acid;

(3) an amino acid substitution at position 71 with arginine and at position 270 with methionine;

(4) an amino acid substitution at position 71 with arginine and at position 300 with aspartic acid;

(5) an amino acid substitution at position 102 with isoleucine and at position 270 with methionine;

(6) an amino acid substitution at position 177 with phenylalanine and at position 220 with valine;

(7) an amino acid substitution at position 226 with glycine and at position 270 with methionine;

(8) an amino acid substitution at position 257 with serine and at position 259 with glutamic acid;

(9) an amino acid substitution at position 257 with serine and at position 270 with methionine;

(10) an amino acid substitution at position 259 with glutamic acid and at position 270 with methionine;

(11) an amino acid substitution at position 259 with glutamic acid and at position 300 with aspartic acid;

(12) an amino acid substitution at position 267 with proline and at position 270 with methionine;

(13) an amino acid substitution at position 270 with methionine and at position 300 with aspartic acid;

(14) an amino acid substitution at position 2 with isoleucine, at position 259 with glutamic acid, and at position 270 with methionine;

(15) an amino acid substitution at position 45 with aspartic acid, at position 175 with aspartic acid, and at position 183 with threonine;

(16) an amino acid substitution at position 102 with isoleucine, at position 226 with glycine, and at position 267 with proline;

(17) an amino acid substitution at position 124 with leucine, at position 259 with glutamic acid, and at position 270 with methionine;

(18) an amino acid substitution at position 177 with phenylalanine, at position 259 with glutamic acid, and at position 270 with methionine;

(19) an amino acid substitution at position 220 with valine, at position 259 with glutamic acid, and at position 270 with methionine;

(20) an amino acid substitution at position 236 with asparagine, at position 259 with glutamic acid, and at position 270 with methionine;

(21) an amino acid substitution at position 238 with isoleucine, at position 259 with glutamic acid, and at position 270 with methionine;

(22) an amino acid substitution at position 257 with serine, at position 259 with glutamic acid, and at position 270 with methionine;

(23) an amino acid substitution at position 257 with serine, at position 259 with glutamic acid, and at position 300 with aspartic acid;

(24) an amino acid substitution at position 259 with glutamic acid, at position 265 with lysine, and at position 270 with methionine;

(25) an amino acid substitution at position 259 with glutamic acid, at position 270 with methionine, and at position 300 with aspartic acid;

(26) an amino acid substitution at position 259 with glutamic acid, at position 270 with methionine, and at position 301 with cysteine;

(27) an amino acid substitution at position 2 with isoleucine and at position 238 with isoleucine;

(28) an amino acid substitution at position 71 with asparagine and at position 195 with leucine;

(29) an amino acid substitution at position 109 with glycine and at position 331 with phenylalanine;

(30) an amino acid substitution at position 124 with leucine and at position 236 with asparagine;

(31) an amino acid substitution at position 159 with phenylalanine and at position 259 with glutamic acid;

(32) an amino acid substitution at position 42 with arginine, at position 155 with arginine, and at position 279 with arginine;

(33) an amino acid substitution at position 45 with aspartic acid, at position 175 with aspartic acid, and at position 183 with threonine;

(34) an amino acid substitution at position 155 with leucine, at position 250 with proline, and at position 298 with proline; and

(35) an amino acid substitution at position 56 with lysine, at position 138 with asparagine, at position 190 with serine, and at position 254 with asparagine.

Moreover, from the standpoint of enhancing the resistance to the reaction inhibition by an organic solvent, the polypeptide of the present invention preferably contains one or more of the following amino acid substitutions relative to the amino acid sequence of SEQ ID NO:1 in the sequence listing:

substitutions at position 22 with arginine, at position 39 with arginine, at position 51 with alanine, at position 87 with isoleucine, at position 90 with glycine, at position 259 with glutamic acid, and at position 270 with methionine.

Further, the polypeptide more preferably contains any of the following amino acid substitutions (1) to (7) relative to the amino acid sequence of SEQ ID NO:1 in the sequence listing:

(1) an amino acid substitution at position 22 with arginine;

(2) an amino acid substitution at position 22 with arginine and at position 87 with isoleucine;

(3) an amino acid substitution at position 39 with arginine;

(4) an amino acid substitution at position 39 with arginine and at position 51 with alanine;

(5) an amino acid substitution at position 51 with alanine;

(6) an amino acid substitution at position 87 with isoleucine; and (7) an amino acid substitution at position 90 with glycine.

The organic solvent is, for example, preferably dimethylformamide, dimethyl sulfoxide, 2-propanol, ethyl acetate, toluene, methanol, ethanol, n-butanol, hexane, acetonitrile, propyl acetate, butyl acetate, acetone, dimethoxypropane, t-methyl butyl ether, diethyl ether, diisopropyl ether, dioxane, tetrahydrofuran, dimethylacetamide, diglyme, ethylene glycol, dimethoxyethane, carbon tetrachloride, methylene chloride, ethylcellosolve, cellosolve acetate, 1,3-dimethyl-2-imidazolidinone, or hexamethylphosphoric triamide, and is more preferably dimethylformamide, dimethyl sulfoxide, 2-propanol, ethyl acetate, toluene, butyl acetate, or 1,3-dimethyl-2-imidazolidinone, and still more preferably dimethylformamide, dimethyl sulfoxide, or 2-propanol.

The enzyme of the present invention has high reactivity to a carbonyl compound even in the presence of an organic solvent. The term "in the presence of an organic solvent" may mean a miscible mixture of a liquid containing the enzyme and an organic solvent, or a heterogeneous mixture of a liquid containing the enzyme and an organic solvent, which may be mixed by physical stirring.

The "enzyme having high reactivity in the presence of an organic solvent" means that the enzyme has higher activity for 2-pentanone reduction in the presence of an organic solvent or after it is held in the presence of the organic solvent for a certain period of time than the wild-type enzyme of SEQ ID NO:1 in the sequence listing. It is preferably an enzyme having high stability to an organic solvent or having high resistance to the reaction inhibition by an organic solvent.

What is meant by "having better stability to an organic solvent" is that, specifically, when the residual activity toward 2-pentanone or 2-hexanone of the enzyme after incubation with an organic solvent is measured by the method described later in Example 4 or 5, the enzyme has a higher residual activity than the wild-type enzyme by at least 1%, preferably by at least 5%, more preferably by at least 10%, and still more preferably by at least 20%.

Moreover, what is meant by "having better resistance to the reaction inhibition by an organic solvent" is that, specifically, when the relative activity toward 2-hexanone in the presence of an organic solvent is measured by the method described later in Example 31, the enzyme has a higher relative activity than the wild-type enzyme by at least 1%, preferably by at least 5%, more preferably by at least 7%, still more preferably by at least 10%, and most preferably by at least 20%.

The stability of the enzyme to an organic solvent can be evaluated, for example, as follows.

[Method for Evaluation of Stability of Enzyme to Organic Solvent]

A buffer (preferably a 0.01 to 1M phosphate buffer with a pH of 5 to 8) containing an organic solvent with a given concentration (e.g. 0.5% to 50%) is added to a cell-free extract containing the enzyme, and the mixture is incubated at a given temperature (e.g. 4 to 40° C.). If the mixture of the organic solvent and the buffer is heterogeneous, the resultant mixture is incubated with shaking or stirring. A sample without the organic solvent and a treated mixture with the organic solvent are each sampled after 0.1 to 48 hours, and then diluted with a 0.1M potassium phosphate aqueous solution (pH 7.0). Using the diluted solutions, the activity of the enzyme is measured as described in [Method for evaluation of carbonyl compound reducing ability] below. The relative activity can be calculated by the following equation.

Relative activity (%)=[enzyme activity in the presence of solvent]/[enzyme activity in the absence of solvent]×100

The altered carbonyl reductase having better stability to an organic solvent than the carbonyl reductase of SEQ ID NO:1 in the sequence listing refers to an enzyme having a higher residual activity as evaluated as above than the wild-type by at least 1%, preferably by at least 5%, more preferably by at least 10%, and most preferably by at least 20%.

[Method for Evaluation of Carbonyl Compound Reducing Ability]

The progress of the reduction reaction can be easily evaluated by reacting at 30° C. a 100 mM potassium phosphate buffer (pH 6.5) with a reaction mixture containing 0.25 mM NADPH or reduced nicotinamide adenine dinucleotide (hereinafter, NADH), 1 to 50 mM of a carbonyl compound to be evaluated for reduction activity (e.g., 2-pentanone, 2-hexanone, 2,3-butanedione), and the polypeptide of the present invention; and measuring the decrease in the absorbance at a wavelength of 340 nm associated with a reduction in the amount of NADPH or NADH. If the absorbance decreases, the polypeptide of the present invention is determined to have an ability to reduce the target carbonyl compound. It is considered that a higher rate of decrease in absorbance indicates a higher ability to reduce the target carbonyl compound. The reducing ability of the polypeptide can also be expressed numerically, and 1 U of reduction activity is defined as the amount of enzyme catalyzing the consumption of 1 μmol of NADPH per minute.

Moreover, the resistance to the reaction inhibition by an organic solvent can be determined, for example, as follows.

[Method 1 for Evaluation of Resistance to Reaction Inhibition by Organic Solvent]

The conversion ratio from a carbonyl compound to an alcohol is determined by reacting a 100 mM potassium phosphate buffer (pH 6.5) with a reaction mixture containing 3 mM NADPH or reduced nicotinamide adenine dinucleotide (hereinafter, NADH), 1% of a carbonyl compound to be evaluated for reduction activity (e.g., 2-pentanone, 2-hexanone, 2,3-butadione), 0.01 to 60% (v/v) of an organic solvent or no organic solvent, and the polypeptide of the present invention at 30° C. for 0.01 to 5 hours; and analyzing the reaction product by, for example, gas chromatography.

The relative activity can be calculated by the following equation.

Relative activity (%)=[conversion ratio in the presence of organic solvent]/[conversion ratio in the absence of organic solvent]×100

As used herein, the altered carbonyl reductase having better resistance to the reaction inhibition by an organic solvent than the carbonyl reductase of SEQ ID NO:1 in the sequence listing means that it has a higher residual activity as evaluated as above than the wild-type by at least 1%, preferably by at least 5%, more preferably by at least 7%, still more preferably by at least 10%, and most preferably by at least 20%. Also, the enzyme of the present invention has higher thermal stability than the carbonyl reductase of SEQ ID NO:1 in the sequence listing.

The altered carbonyl reductase of the present invention can be searched as follows.

DNA fragments in which one or more base sequence substitutions, insertions, deletions, and/or additions are introduced into the base sequence (wild-type enzyme gene) of SEQ ID NO:2 in the sequence listing can be obtained by using error-prone PCR (Leung et al., Technique 1, 11-15 (1989)) or a kit based on the same principle. For example, using the wild-type enzyme gene as a template, T at position 240 can be substituted by C by usual techniques, so that the NdeI recognition site can be destroyed without a change in the amino acid sequence of the wild-type enzyme (SEQ ID NO:3 in the sequence listing). Using the resulting sequence as a template, a pair of primer 1: 5'-GGGAATTCCATATGAGTGTTTTAGTTACAGG-3' (SEQ ID NO:4 in the sequence listing) and primer 2: 5'-ATACGCGTCGACTTACTATTGTTCTTGAACCTTCA-3' (SEQ ID NO:5 in the sequence listing), and Diversify PCR Random Mutagenesis Kit (from Clontech), multiple kinds of double-stranded DNAs (mutant enzyme genes) can be obtained in which a mutation is introduced randomly into the full length of the gene encoding the wild-type enzyme, a NdeI recognition site is added to the initiation codon, and a SalI recognition site is added immediately after the termination codon. Amplified fragments of the DNAs are digested with NdeI and SalI, and then inserted between the NdeI recognition site and the SalI recognition site downstream from the lac promoter in the plasmid pUCN18 (a plasmid obtained by changing T at position 185 in pUC18 (from Takara Bio, Inc.) to A to destroy the NdeI site, and further changing GC at positions 471 and 472 to TG to introduce a new NdeI site by PCR). The resulting plasmid is used to transform *Escherichia coli* HB101 (hereinafter, *E. coli* HB101). The transformed *E. coli* is applied to an LB medium plate containing 100 μg/mL ampicillin to obtain a single colony of *E. coli*. Moreover, using mutant enzyme genes prepared as above in place of the wild-type gene, mutations can be further introduced by the same procedures to prepare a mutant enzyme library.

From the library, altered carbonyl reductases according to the present invention can be selected. The selection method is not particularly limited, but the following method is preferred.

[Selection Method 1 by Plate Evaluation of Enzyme Having Better Stability to Organic Solvent]

Recombinant bacteria from the mutant enzyme library and a recombinant bacterium producing the wild-type enzyme (e.g. *E. coli* HB101 (pNKP) in Reference Example 3) are each inoculated into an appropriate medium (e.g. 2×YT medium (1.6% tryptone, 1.0% yeast extract, and 0.5% sodium chloride, pH 7.0) containing 200 μg/ml ampicillin) and cultured with shaking at 37° C. for 24 hours. The cells in the obtained culture media are disrupted and centrifuged, followed by removing the precipitate to obtain a cell-free extract. A buffer (preferably a 0.01 to 1M phosphate buffer with a pH of 5 to 8) containing an organic solvent having an appropriate concentration (preferably dimethylformamide having a final concentration of 10 to 30%) is added to the cell-free extracts containing the respective enzymes, followed by incubation at an appropriate temperature (e.g. 4 to 40° C.). After incubation for about 0.1 to 48 hours, the treated cell-free extracts are dispensed into a 96-well plate (from AGC Techno Glass Co., Ltd.). A phosphate buffer (pH 5 to 7) containing NADPH (preferably 1.5 mM) and a carbonyl compound (preferably 10 mM 2,3-butanedione) is added and they are reacted at 10° C. to 40° C. NADPH fluorescence is measured with time using an UV transilluminator and recording system FAS-III (from Toyobo Co., Ltd.). At this time, an enzyme solution in which the reaction does not proceed shows the remaining NADPH fluorescence, while a cell-free extract in which the reaction has proceeded shows reduced fluorescence with the decrease in NADPH. Enzymes which show quenched fluorescence in a short time compared to the wild-type enzyme (control) are selected as enzymes having better stability to a chloride. Plasmids are extracted from the culture media containing the selected enzymes, and the base sequence of the altered carbonyl reductase genes is determined using BigDye Terminator Cycle Sequencing Kit (from Applied Biosystems Japan, Ltd.) and Applied Biosystems 3130xl Genetic Analyzer (from Applied Biosystems Japan, Ltd.), whereby the mutation sites can be identified.

[Selection Method 2 by Plate Evaluation of Enzyme Having Better Stability to Organic Solvent]

Recombinant bacteria from the mutant enzyme library and a bacterium producing the wild-type enzyme (e.g. *E. coli* HB101 (pNKP) in Reference Example 3) are each inoculated into an appropriate agar medium (e.g. an LB medium plate containing 100 μg/mL ampicillin) and cultured at 30° C. for 24 hours. The thus obtained colonies are transferred to a nylon membrane (Biodyne A, 0.45 μm), which is then immersed in a buffer (preferably 50 mM 3-(N-morpholino)propanesulfonic acid (MOPS) buffer) containing an organic solvent (preferably 40% dimethylformamide) for 0.1 minutes to 24 hours. This buffer has preferably been heated to 40° C. to 80° C. Then the nylon membrane is immersed in a buffer (preferably 50 mM 3-(N-morpholino)propanesulfonic acid (MOPS) buffer) containing NADP$^+$ (preferably 1 mM), nitroblue tetrazolium (preferably 200 µM), 1-methoxy-5-methylphenazinium methylsulfate (preferably 10 µM), and 2-propanol (e.g. 0.1 to 50%) at an appropriate temperature (e.g. 4 to 40° C.) for 0.1 minutes to 24 hours. Thereafter, the nylon membrane is washed with distilled water, whereby four-color stained colonies can be selected as recombinant bacteria with altered carbonyl reductases having better stability to an organic solvent.

These recombinant bacteria are each inoculated into an appropriate liquid medium (e.g. 2×YT medium (1.6% tryptone, 1.0% yeast extract, and 0.5% sodium chloride, pH 7.0) containing 200 µg/ml ampicillin) and cultured with shaking at 37° C. for 20 hours. The cells in the obtained culture media are collected by centrifugation and suspended in a buffer (preferably 50 mM 3-(N-morpholino)propanesulfonic acid (MOPS) buffer). The suspension is disrupted with a model UH-50 ultrasonic homogenizer (from SMT), followed by removing the cell debris by centrifugation to obtain a cell-free extract.

A mixture of a buffer (preferably 50 mM 3-(N-morpholino)propanesulfonic acid (MOPS) buffer) and dimethylformamide is added to the cell-free extracts to give a final concentration of dimethylformamide of preferably 0.1 to 60%, followed by heating (preferably at 40° C. to 80° C. for 0.1 minutes to 24 hours) and then cooling with ice. The cooled mixtures are each mixed with a buffer (preferably 50 mM 3-(N-morpholino)propanesulfonic acid (MOPS) buffer) containing NADP$^+$ (preferably 1 mM), nitroblue tetrazolium (preferably 200 µM), 1-methoxy-5-methylphenazinium methylsulfate (preferably 10 µM), and 2-propanol (e.g. 0.1 to 50%), and then transferred to a 96-well plate (from AGC Techno Glass Co., Ltd.) and observed. Stained samples can be selected as altered carbonyl reductases having better stability to an organic solvent.

Plasmids are extracted from the culture media of the selected recombinant bacteria, and the base sequence of the mutant RKP genes (RKP being a polypeptide having activity for the reduction of a carbonyl compound) is determined using BigDye Terminator Cycle Sequencing Kit (from Applied Biosystems Japan, Ltd.) and Applied Biosystems 3130xl Genetic Analyzer (from Applied Biosystems Japan, Ltd.), whereby the mutation sites can be identified.

[Selection Method by Plate Evaluation of Enzyme Having Better Resistance to Reaction Inhibition by Organic Solvent]

Recombinant bacteria from the mutant enzyme library and a bacterium producing the wild-type enzyme (e.g. *E. coli* HB101 (pNKP) in Reference Example 3) are each inoculated into an appropriate agar medium (e.g. an LB medium plate containing 100 µg/mL ampicillin) and cultured at 30° C. for 24 hours. The thus obtained colonies are transferred to a nylon membrane (Biodyne A, 0.45 µm), which is then immersed into a buffer (preferably 50 mM 3-(N-morpholino)propanesulfonic acid (MOPS) buffer) containing NADP$^+$ (preferably 1 mM), nitroblue tetrazolium (preferably 200 µM), 1-methoxy-5-methylphenazinium methylsulfate (preferably 10 µM), 2-propanol (e.g. 0.1 to 50%), and an organic solvent (preferably 0.1 to 80% dimethylformamide) at an appropriate temperature (e.g., 4 to 40° C.) for 0.1 minutes to 10 hours. Thereafter, the nylon membrane is washed with distilled water, and then stained colonies can be selected as candidates for recombinant bacteria with altered carbonyl reductases having better resistance to the reaction inhibition by an organic solvent.

These recombinant bacteria are each inoculated into an appropriate liquid medium (e.g. 2×YT medium (1.6% tryptone, 1.0% yeast extract, and 0.5% sodium chloride, pH 7.0) containing 200 µg/ml ampicillin) and cultured with shaking at 37° C. for 20 hours. The cells in the obtained culture media are disrupted and centrifuged, followed by removing the precipitate to obtain a cell-free extract. The cell-free extracts are each mixed with a buffer (preferably 0.1M phosphate buffer (pH 6.5)) containing NADPH (preferably 0.625M), a carbonyl compound (preferably 10 mM 2,3-butanedione), and an organic solvent (preferably 0.1 to 80% dimethylformamide) dissolved therein. The mixtures are dispensed into a 96-well plate (from Asahi Techno Glass), and NADPH fluorescence is measured with time using a Benchmark Plus microplate spectrophotometer (from BIO-RAD). An enzyme solution in which the reaction does not proceed shows the remaining NADPH fluorescence, while a cell-free extract in which the reaction has proceeded shows reduced fluorescence with the decrease in NADPH. Samples in which NADPH is consumed due to the reduction of the carbonyl compound and thus fluorescence is quenched in a short time are selected as recombinant bacteria with altered carbonyl reductases having even better resistance to the reaction inhibition by an organic solvent.

Plasmids are extracted from the culture media of the selected recombinant bacteria, and the base sequence of the mutant RKP genes is determined using BigDye Terminator Cycle Sequencing Kit (from Applied Biosystems Japan, Ltd.) and Applied Biosystems 3130xl Genetic Analyzer (from Applied Biosystems Japan, Ltd.), whereby the mutation sites can be identified.

Altered carbonyl reductases having combined properties of multiple mutations can be produced using site-directed mutagenesis by combining multiple mutations which can enhance reactivity to a carbonyl compound in the presence of an organic solvent and/or thermal stability.

The polynucleotide of the present invention may be any polynucleotide encoding the polypeptide of the present invention. Examples include a polynucleotide having a base sequence encoding the wild-type enzyme of SEQ ID NO:2 in the sequence listing, and polypeptides obtainable by modifying the polynucleotide.

The wild-type enzyme gene can be modified by known methods described in Current Protocols in Molecular Biology (Frederick M. Ausubel, Greene Publishing Associates and Wiley-Interscience (1989)) and the like. Specifically, polynucleotides in which the amino acid sequence of the wild-type enzyme is altered can be produced by substitution, addition, insertion, or deletion of one or more bases (e.g., 40, preferably 20, more preferably 10, still more preferably 5, 4, 3, or 2 bases) of the wild-type enzyme gene. Examples include mutagenesis methods based on PCR such as error-prone PCR (Leung et al., Technique 1, 11-15 (1989)), and methods using commercially available kits such as Diversify PCR Random Mutagenesis Kit (from Clontech), Transformer Mutagenesis Kit (from Clontech), EXOIII/Mung Bean Deletion Kit (from Stratagene), or QuickChange Site Directed Mutagenesis Kit (from Stratagene).

When a polynucleotide is produced by site-directed mutagenesis, the site-directed mutagenesis is carried out by, for example, the methods reported by Olfert Landt et al. (Gene, 96, 125-128 (1990)); Smith et al. (Genetic Engineering, 3, 1, Setlow, J. Plenum Press); Vlasuk et al. (Experimental Manipulation of Gene Expression, Inouye, M. Academic Press); and Hos. N. Hunt et al. (Gene, 77, 51 (1989)), or using commercially available kits such as QuikChange II Kit (from Stratagene). In the case of mutation at two positions, the target polynucleotide of the present invention can be obtained by repeating a method based on any of the above methods twice. Also in the case that the amino acids at other positions are substituted by other amino acids, the target polynucleotide of the present invention can be obtained in this manner.

The polynucleotide encoding the polypeptide of the present invention is preferably a polynucleotide that encodes a polypeptide having activity in reducing 2-pentanone to 2-pentanol and having higher reactivity to a carbonyl compound in the presence of an organic solvent than a carbonyl reductase having the amino acid sequence of SEQ ID NO:1 in the sequence listing, and that hybridizes under stringent conditions with a polynucleotide containing a base sequence complementary to a polynucleotide having the base sequence of SEQ ID NO:2 in the sequence listing.

The "polynucleotide that hybridizes under stringent conditions with a polynucleotide having a base sequence complementary to the polynucleotide of SEQ ID NO:2 in the sequence listing" means a polynucleotide obtained using as a probe a polynucleotide having a base sequence complementary to the base sequence of SEQ ID NO:2 in the sequence listing by colony hybridization, plaque hybridization, Southern hybridization or the like under stringent conditions.

The hybridization can be carried out in accordance with the methods described in Molecular Cloning 2nd Edition (Joseph Sambrook, Cold Spring Harbor Laboratory Press (1989)) and the like. The "polynucleotide that hybridizes under stringent conditions" may be, for example, a DNA obtained by hybridizing the polynucleotide derived from a colony or plaque fixed on a filter at 65° C. in the presence of 0.7 to 1.0M sodium chloride, and then washing the filter at 65° C. with 3×SSC solution (1 SSC solution contains 150 mM sodium chloride and 15 mM sodium citrate). The polynucleotide is more preferably obtained by washing with 1 SSC solution at 65° C., still more preferably with 0.7×SSC solution at 65° C., and even more preferably with 0.5×, 0.45×, 0.25×, 0.2×, or 0.15×SSC solution at 65° C.

The hybridization conditions are not particularly limited to those described above. Several factors, such as temperature and salt concentration, are thought to affect the stringency of hybridization, and those skilled in the art can select appropriate conditions for such factors to achieve optimal stringency.

The polynucleotide hybridizable under the above conditions may be, for example, preferably a polynucleotide having at least 78%, more preferably at least 84%, still more preferably at least 87%, and even more preferably at least 89%, at least 90%, at least 94%, at least 95%, or at least 97% sequence identity to the polynucleotide of SEQ ID NO:2. Any polynucleotide encoding a polypeptide that has the properties of the polypeptide of the present invention is included in the above polynucleotide.

A polypeptide-expressing vector can be constructed by inserting the polynucleotide encoding the polypeptide of the present invention into an expression vector.

The expression vector used in the above process may be any vector that can express the polypeptide encoded by the polynucleotide in an appropriate host organism. Examples of such vectors include plasmid vectors, phage vectors, and cosmid vectors. Also, shuttle vectors that enable gene exchange to occur between one host strain and another can also be used.

Such a vector for *Escherichia coli*, for example, usually contains a regulatory element such as a lacUV5 promoter, a trp promoter, a trc promoter, a tac promoter, a lpp promoter, a tufB promoter, a recA promoter, or a pL promoter and is suitable as an expression vector containing an expression unit operably linked to the DNA of the present invention. Examples include pUCN18 (see Reference Example 2), pSTV28 (from Takara Bio Inc.), and pUCNT (WO 94/03613).

The term "regulatory element" as used herein refers to a base sequence containing a functional promoter and any related transcription element(s) (e.g., an enhancer, CCAAT box, TATA box, SPI site, or the like).

The term "operably linked" as used herein means that various regulatory elements (e.g., a promoter, enhancer, and the like) regulating the expression of the gene are linked to the gene such that they can work in host cells. It is well known to ones having ordinary skill in the art that the type and kind of regulatory element may vary depending on the host.

Vectors, promoters and the like which can be used in various organisms are described in detail in "Biseibutsugaku Kiso Koza (Basic Courses in Microbiology) (8, Tadahiko ANDO, Kyoritsu Shuppan, 1987)", and the like.

The vector may further contain a polynucleotide that encodes a polypeptide capable of regenerating a reduced coenzyme. Examples of the polypeptide capable of regenerating a reduced coenzyme include glucose dehydrogenase.

A transformant can be obtained by transforming a host cell with the vector. The transformant may also be obtained by introducing the polynucleotide that encodes the polypeptide of the present invention into the chromosome.

The host cell to be transformed with the vector may be any cell that can be transformed with the polypeptide-expressing vector containing the polynucleotide encoding the polypeptide, so as to express the polypeptide encoded by the introduced polynucleotide. Examples of microorganisms that can be used as the host cell include bacteria for which host-vector systems have been developed, such as those belonging to the genera *Escherichia, Bacillus, Pseudomonas, Serratia, Brevibacterium, Corynebacterium, Streptococcus,* and *Lactobacillus*; actinomycetes for which host-vector systems have been developed, such as those belonging to the genera *Rhodococcus* and *Streptomyces*; yeasts for which host-vector systems have been developed, such as those belonging to the genera *Saccharomyces, Kluyveromyces, Schizosaccharomyces, Zygosaccharomyces, Yarrowia, Trichosporon, Rhodosporidium, Pichia,* and *Candida*; and molds for which host-vector systems have been developed, such as those belonging to the genera *Neurospora, Aspergillus, Cephalosporium,* and *Trichoderma*. Besides microorganisms, various host-vector systems have also been developed for plants and animals. In particular, systems for expressing a large amount of heterologous protein in an insect such as a silkworm (Nature, 315, 592-594 (1985)), or a plant such as a rape, corn, or potato have been developed, which can be suitably used. Among these, preferred in view of the efficiency in introduction and expression are bacteria, with *E. coli* being particularly preferred.

The vector of the present invention can be introduced into host microorganisms by known methods. For example, in the case that the polypeptide-expressing vector is any of plasmids of the present invention (pNKPm01 to pNKPm53 in Examples 2, 3, 6 to 15, 17 to 27, and 30) obtained by introducing a polynucleotide encoding an altered carbonyl reductase into the above expression vector pUCN18, and the host microorganism is *E. coli*, a transformant (e.g. *E. coli* HB101 (pNKPm50) in Example 27) can be obtained by engineering commercially available *E. coli* HB101 competent cells (from Takara Bio, Inc.) or the like according to the protocol provided with the cells to introduce the vector into the host cell.

Also, a transformant can be grown which is transformed to express both the polypeptide of the present invention and the polypeptide capable of regenerating a reduced coenzyme described later in the same cell. Specifically, a transformant can be obtained by incorporating the polynucleotide encoding the polypeptide of the present invention and the polynucleotide encoding a polypeptide capable of regenerating a reduced coenzyme into the same vector, and introducing the vector into the host cell. Or alternatively, it can be obtained by incorporating these two kinds of DNAs into the respective two vectors from different incompatibility groups, and introducing the vectors into the same host cell.

Examples of transformants that can be obtained as described above include a transformant obtained by introducing into *E. coli* HB101 competent cells (from Takara Bio, Inc.) both a recombinant vector (e.g. pNKPm01 in Example 2) obtained by introducing the nucleotide encoding the altered carbonyl reductase into the expression vector pUCN18, and a vector containing a polynucleotide encoding glucose dehydrogenase which is a polypeptide capable of regenerating a reduced coenzyme.

The polypeptide of the present invention or the transformant and/or a treated product thereof can be allowed to act on a carbonyl compound to produce an alcohol compound.

The carbonyl compound used as a substrate is not particularly limited. Among carbonyl compounds, unsymmetrical ketones are preferred because they are reduced into useful optically active alcohols.

Examples of such carbonyl group-containing compounds include unsymmetrical ketones represented by the following formula (1):

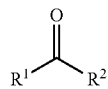

(1)

wherein $R^1$ and $R^2$ are each a hydrogen atom, a halogen atom, an optionally substituted alkyl group, an optionally substituted aralkyl group, an optionally substituted aryl group, an optionally substituted alkoxy group, an amino group, or a nitro group, or $R^1$ and $R^2$ may be joined together to form a ring, provided that $R^1$ and $R^2$ have different structures. Examples of the products formed therefrom include optically active alcohols represented by the following formula (2):

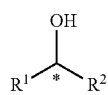

(2)

wherein $R^1$ and $R^2$ are the same as described above, and * represents an asymmetric carbon atom.

The $R^1$ and $R^2$ are each preferably a C1 to C14 alkyl group, a C6 to C14 aryl group, a C4 to C14 heteroaryl group, a C1 to C5 alkoxy group, a C2 to C5 alkoxycarboxyl group, a C1 to C5 linear or branched alkyl group, a C2 to C5 alkenyl group, a C5 to C10 cycloalkyl group, a C4 to C9 heterocycloalkyl group, a carboxyl group, a hydrogen atom, a halogen atom, a hydroxyl group, an amino group, or a nitro group.

The term "optionally substituted" means that the group may have a substituent. Examples of the substituent include halogen atoms and hydroxyl, carboxyl, amino, cyano, nitro, alkyl, aryl, aralkyl, and alkoxy groups. Examples of halogen atoms include fluorine, chlorine, bromine, and iodine atoms.

Specific example of the carbonyl compound include 2-pentanone, 2-hexanone, 2,3-butanedione, acetophenone, (S)-1-(4-fluoro-phenyl)-5-(2-oxo-4-phenyl-oxazolidin-3-yl)-pentane-1,5-dione, propiophenone, n-butyrophenone, valerophenone, hexanophenone, 1-phenyl-2-butanone, benzylacetone, 2,5-hexanedione, 2,3-hexanedione, 3,4-hexanedione, and phenoxy-2-propanone.

Examples of the alcohol compound produced using the polypeptide of the present invention include 2-pentanol, 2-hexanol, 2,3-butanediol, 3-hydroxy-2-butanone, 1-phenyl ethyl alcohol, [3-[(5R)-(4-fluoro-phenyl)-5-hydroxypentanoyl]-(4S)-phenyl-1,3-oxazolidin-2-one, 1-phenyl-1-propanol, 1-phenyl-1-butanol, 1-phenyl-1-pentanol, 1-phenyl-1-hexanol, 1-phenyl-2-butanol, 4-phenyl-2-butanol, 2,5-hexanediol, 5-hydroxy-2-hexanone, 2,3-hexanediol, 2-hydroxyhexan-3-one, 3-hydroxy-2-hexanone, 3,4-hexanediol, 4-hydroxy-3-hexanone, and 1-phenoxy-2-propanol.

When the carbonyl group-containing compound is reduced into an alcohol using the polypeptide of the present invention or the transformant expressing the polypeptide of the present invention and/or a treated product thereof, the following procedure may be followed. However, the procedure is not limited to the following procedure.

An appropriate solvent (e.g. 100 mM phosphate buffer (pH 6.5)), a carbonyl compound substrate (e.g. 2-pentanone or acetophenone), a coenzyme such as NADPH or oxidized nicotinamide adenine dinucleotide phosphate (hereinafter, NADP$^+$), and a cultured product of the transformant and/or a treated product or the like thereof are added, and then reacted with stirring while the pH is controlled.

The term "treated product" means a product still having the enzyme catalytic activity of the polypeptide, such as a crude extract, cultured cells, a freeze-dried organism, an acetone-dried organism, disrupted cells, or immobilized preparations thereof.

The reaction temperature is preferably 5° C. to 80° C., more preferably 10° C. to 60° C., and still more preferably 20° C. to 40° C. The pH of the reaction mixture is preferably 3 to 10, more preferably 4 to 9, and still more preferably 5 to 8. The reaction may be carried out either batchwise or in a continuous manner. In the case of the batchwise method, the reaction substrate may be introduced at a concentration of 0.01 to 100% (w/v), preferably 0.1 to 70% (w/v), and more preferably 0.5 to 50% (w/v) of the total reaction mixture. An additional amount of substrate may be further added during the reaction.

Moreover, in the reaction, an aqueous solvent may be used, or a mixture of an aqueous solvent and an organic solvent may be used. Examples of the organic solvent include dimethylformamide, dimethyl sulfoxide, 2-propanol, ethyl acetate, toluene, methanol, ethanol, n-butanol, hexane, acetonitrile, propyl acetate, butyl acetate, acetone, dimethoxypropane, t-methyl butyl ether, diethyl ether, diisopropyl ether, dioxane, tetrahydrofuran, dimethylacetamide, diglyme, ethylene glycol, dimethoxyethane, carbon tetrachloride, methylene chloride, ethylcellosolve, cellosolve acetate, 1,3-dimethyl-2-imidazolidinone, and hexamethylphosphoric triamide. The concentration of the organic solvent in the reaction system is not particularly limited, but is preferably 1 to 95%, more preferably 5 to 90%, and still more preferably 10 to 80%.

The treated product or the like of the transformant refers to, for example, a cell-free extract, cultured cells, freeze-dried cells, acetone-dried cells, disrupted products thereof, or mixtures thereof. Moreover, they may be used after the polypeptide itself or directly the cells are immobilized by known means.

Moreover, in the reaction, a transformant producing both the polypeptide of the present invention and a polypeptide capable of regenerating a reduced coenzyme can be used to greatly reduce the amount of coenzyme used. The polypeptide capable of regenerating a reduced coenzyme is described in detail below.

When an alcohol compound is synthesized by reducing a carbonyl compound using the transformant capable of producing the polypeptide of the present invention, NADPH or NADH is required as a coenzyme. As described above, the reduction reaction can be carried out by adding a required amount of NADPH or NADH to the reaction system. However, the amount of expensive coenzyme can be greatly reduced by carrying out the reaction using the polypeptide of the present invention in combination with a coenzyme regeneration system that contains an enzyme capable of converting the coenzyme (NADP$^+$ or NAD$^+$) in oxidized form into reduced NADPH or NADH (hereinafter, such an ability is referred to as a reduced-coenzyme regeneration ability), and a substrate thereof. The enzyme having the reduced-coenzyme regeneration ability may be, for example, hydrogenase, formic acid dehydrogenase, carbonyl reductase, glucose-6-phosphate dehydrogenase, or glucose dehydrogenase. Suitable is glucose dehydrogenase.

The reaction may be carried out by adding the coenzyme regeneration system to an asymmetric reduction reaction system. However, when the catalyst used is a transformant obtained by transformation with both the polynucleotide encoding the enzyme of the present invention and a polynucleotide encoding the polypeptide capable of regenerating a reduced coenzyme, the reaction can be efficiently performed without separately preparing the enzyme capable of regenerating a reduced coenzyme and adding the prepared enzyme into the reaction system. Such a transformant can be obtained by the above-described method for preparing a transformant.

After the reaction, an alcohol can be recovered from the reaction mixture by any method, such as by extracting the alcohol directly from the reaction mixture or, if necessary, after separating cells and the like, with a solvent such as ethyl acetate, toluene, t-butyl methyl ether, hexane, or methylene chloride, followed by dehydration and then purification by distillation, recrystallization, silica gel column chromatography, or the like. A high purity alcohol compound can be easily obtained by this method.

EXAMPLES

The following examples illustrate the present invention in detail. They are, however, by no means limitative of the invention. The recombinant DNA technology procedures and the like used in the examples below are described in detail in the following textbooks: Molecular Cloning 2nd Edition (Joseph Sambrook, Cold Spring Harbor Laboratory Press (1989)), and Current Protocols in Molecular Biology (Frederick M. Ausubel, Greene Publishing Associates and Wiley-Interscience (1989)).

(Reference Example 1) Acquisition of DNA Encoding Polypeptide (Wild-Type Enzyme) Having Activity for Carbonyl Compound Reduction Derived from *Vanderwaltozyma polyspora* NBRC 0996

A DNA encoding a polypeptide having activity for the reduction of a carbonyl compound (hereinafter, the polypeptide is referred to as RKP) was obtained by PCR from *Vanderwaltozyma polyspora* NBRC 0996.
[Preparation of Chromosomal DNA from *Vanderwaltozyma polyspora* NBRC 0996]

In a 500-ml Sakaguchi flask, 50 ml of a liquid medium (pH 7) containing 16 g of bacto-tryptone, 10 g of yeast extract, 5 g of sodium chloride, and 0.1 g of Adekanol LG-109 (from NOF Corporation) (each per liter) was prepared and steam sterilized at 120° C. for 20 minutes. The medium was inoculated with 5 ml of a culture of *Vanderwaltozyma polyspora* NBRC 0996 precultured in the same medium in advance, and the strain was cultured with shaking at 30° C. for 18 hours. A chromosomal DNA was extracted from the culture medium according to the method of Murray et al. (Nucl. Acids Res. 8, 4321 (1980)).
[PCR Reaction]

PCR was performed using primer 1: 5'-GGGAATTC-CATATGAGTGTTTTAGTTACAGG-3' (SEQ ID NO:4 in the sequence listing) and primer 2: 5'-ATACGCGTCGACT-TACTATTGTTCTTGAACCTTCA-3' (SEQ ID NO:5 in the sequence listing), and the chromosomal DNA of *Vanderwaltozyma polyspora* NBRC 0996 as a template.

As a result, a double-stranded DNA (RKP gene) was obtained which had a NdeI recognition site added to the initiation codon of the gene having the base sequence of SEQ ID No:2 in the sequence listing, and had a SalI recognition site added immediately after the termination codon. PCR was further performed using the obtained DNA as a template, so that T at position 240 was changed to C by usual techniques. Thus, without a change in the amino acid sequence of the RKP enzyme encoded by the gene, a double-stranded DNA having the base sequence of SEQ ID NO:3 in the sequence listing in which the NdeI recognition site in the gene was destroyed (RKP gene with the NdeI site destroyed) was obtained. The PCR was carried out using PrimeSTAR HS DNA Polymerase (from Takara Bio, Inc.) as a DNA polymerase under reaction conditions as described in the manual.

(Reference Example 2) Construction of Recombinant Vector pNKP

A recombinant vector pNKP was constructed by digesting with NdeI and SalI the RKP gene with the NdeI site destroyed in Reference Example 1, and inserting the fragment between the NdeI recognition site and the SalI recognition site downstream from the lac promoter in the plasmid pUCN18 (a plasmid obtained by changing T at position 185 in pUC18 (from Takara Bio, Inc.) to A to destroy the NdeI site, and further changing GC at positions 471 and 472 to TG to introduce a new NdeI site by PCR).

(Reference Example 3) Production of Recombinant Organism that Expresses Polypeptide Using the recombinant vector pNKP constructed in Reference Example 2, *E. coli* HB101 competent cells (from Takara Bio, Inc.) were transformed to produce a recombinant organism *E. coli* HB101 (pNKP). Also, using the pUCN18, *E. coli* HB101 competent cells (from Takara Bio, Inc.) were transformed to produce a recombinant organism *E. coli* HB101 (pUCN18).

(Reference Example 4) Expression of DNA in Recombinant Organism

The two kinds of recombinant organisms obtained in Reference Example 3 (*E. coli* HB101 (pUCN18), *E. coli* HB101 (pNKP)) were each inoculated into 5 ml of 2×YT medium (1.6% tryptone, 1.0% yeast extract, and 0.5% sodium chloride, pH 7.0) containing 200 μg/ml ampicillin and cultured with shaking at 37° C. for 24 hours. The cells in the culture media obtained above were collected by centrifugation and suspended in 5 ml of 100 mM phosphate buffer (pH 6.5). The suspension was disrupted with a model UH-50 ultrasonic homogenizer (from SMT), followed by removing the cell debris by centrifugation to obtain a cell-free extract. The activity for acetophenone reduction of the thus obtained cell-free extracts was measured. The activity for acetophenone reduction was calculated from the rate of decrease in the absorbance at a wavelength of 340 nm as determined by adding 10 mM acetophenone, 0.25 mM coenzyme NADPH, and the cell-free extract to 100 mM phosphate buffer (pH 6.5) and reacting them at 30° C. for 1 minute. The enzyme activity oxidizing 1 μmol of NADPH to NADP per minute under these reaction conditions was defined as 1 U. The acetophenone-reducing activities of the recombinant organisms are described below. *E. coli* HB101 (pUCN18) showed an acetophenone-reducing activity of 0.1 U/mg or lower, while *E. coli* HB101 (pNKP) which expressed RKP showed an acetophenone-reducing activity of 5 U/mg. As described above, the recombinant organisms obtained in Reference Example 3 were found to have activity for acetophenone reduction and to express RKP.

(Reference Example 5) Stability of Wild-Type Enzyme RKP to Organic Solvent

A cell-free extract of the wild-type enzyme was obtained in the same manner as in Reference Example 4. To the cell-free extract was added dimethylformamide at a final concentration of 30, 40 or 50%, and they were adjusted to a pH of 6.5 using sulfuric acid or sodium hydroxide and then incubated at 30° C. for 3 hours. A cell-free extract to which nothing was added was also similarly incubated as a control. The cell-free extracts were diluted after 3 hours. The 2-pentanone-reducing activity of these cell-free extracts was measured in the same manner as in Reference Example 4. The relative activity with the addition of the solvent was calculated by the equation below and used as an indicator of stability to various compounds. The results are shown in Table 1.

Relative activity (%)=[enzyme activity after just 3 hours (with solvent)]/[enzyme activity after just 3 hours (without solvent)]×100

TABLE 1

| Solvent added | Concentration | Relative activity (%) |
|---|---|---|
| No solvent | | 100 |
| Dimethylformamide | 30% | 64 |
| | 40% | 9 |
| | 50% | 0 |

TABLE 1-continued

| Solvent added | Concentration | Relative activity (%) |
|---|---|---|
| Dimethyl sulfoxide | 40% | 91 |
| | 50% | 58 |

The wild-type enzyme showed lower stability to dimethylformamide than to dimethyl sulfoxide.

(Reference Example 6) Stability of Wild-Type Enzyme RKP to Organic Solvent

A cell-free extract of the wild-type enzyme was obtained in the same manner as in Reference Example 4. To the cell-free extract was added dimethylformamide at a final concentration of 30%, and they were adjusted to a pH of 6.5 using sulfuric acid or sodium hydroxide and then incubated at 30° C. for 2 hours. A cell-free extract to which nothing was added was also similarly incubated as a control. The cell-free extracts were diluted after 2 hours. The 2-hexanone-reducing activity of these cell-free extracts was measured. The rate of decrease in the absorbance at a wavelength of 340 nm was determined by adding 10 mM 2-hexanone, 0.25 mM coenzyme NADPH, and the cell-free extract to 100 mM phosphate buffer (pH 6.5) and reacting them at 30° C. for 1 minute. The 2-hexanone-reducing activity was calculated from the rate of decrease. The relative activity with the addition of the solvent was calculated by the equation below and used as an indicator of stability to various compounds. The activity (relative activity) of the wild-type enzyme with the solvent was 8% of that without the solvent.

Relative activity (%)=[enzyme activity after just 2 hours (with solvent)]/[enzyme activity after just 2 hours (without solvent)]×100

(Reference Example 7) Inhibition of Reaction of Wild-Type Enzyme RKP by Organic Solvent A cell-free extract of the wild-type enzyme was obtained in the same manner as in Reference Example 4. To the cell-free extract was added dimethylformamide at a final concentration of 30%, and they were adjusted to a pH of 6.5 using sulfuric acid or sodium hydroxide and then incubated at 30° C. for 2 hours. A cell-free extract to which nothing was added was also similarly incubated as a control. The cell-free extracts were diluted after 2 hours. The 2-hexanone-reducing activity of these cell-free extracts was measured. A reaction was carried out by adding 30% dimethylformamide, 10 mM 2-hexanone, 0.25 mM coenzyme NADPH, and the cell-free extract to 100 mM phosphate buffer (pH 6.5). The rate of NADPH consumption was determined from the rate of decrease in NADPH fluorescence, whereby the 2-hexanone-reducing activity was calculated. The relative activity with the addition of the solvent was calculated by the equation below and used as an indicator of stability to various compounds. The activity (relative activity) of the wild-type enzyme with the solvent was 24% of that without the solvent.

Relative activity (%)=[enzyme activity (with solvent)]/[enzyme activity (without solvent)]×100

(Example 1) Preparation 1 of Mutant Enzyme Library

DNA amplified fragments in which a mutation was introduced randomly into the full length of the RKP gene were obtained by error-prone PCR (Leung et al. Technique 1, 11-15 (1989)) using the plasmid pNKP containing the RKP gene prepared in Reference Example 2 as a template, primer 1: 5'-GGGAATTCCATATGAGTGTTTTAGTTACAGG-3' (SEQ ID NO:4 in the sequence listing), and primer 2: 5'-ATACGCGTCGACTTACTATTGTTCTTGAACCT-TCA-3' (SEQ ID NO:5 in the sequence listing). The amplified fragments were digested with the restriction enzymes NdeI and SalI and then incorporated into a high expression vector pUCN18 treated with the same enzymes to prepare mutant-enzyme-expressing plasmids. With each plasmid, *E. coli* HB101 was transformed, and the transformant was applied to an LB medium plate containing 100 µg/mL ampicillin. The colonies grown in each case were formed of a recombinant *E. coli* containing a mutated RKP gene. The group of these recombinant bacteria is referred to as mutant enzyme library 1.

(Example 2) Selection 1 of Altered Carbonyl Reductase

Altered carbonyl reductases having better stability to an organic solvent were selected from the mutant enzyme library 1. The recombinant bacteria in the mutant enzyme library 1 prepared in Example 1 and *E. coli* HB101 (pNKP) (control) prepared in Reference Example 3 were each cultured in the same manner as in Reference Example 4. To 60 µL of each of the obtained culture media was added 240 µL of phosphate buffer (pH 7.0) containing 10 mM EDTA·2Na and 1% Triton X-100, and the mixture was incubated at 37° C. for 1 hour. The treated media were centrifuged to give a supernatant as a cell-free extract. Phosphate buffer (pH 6.5) containing dimethylformamide at a final concentration of 10 to 30% was added to 200 µL of each of the cell-free extracts, followed by incubation at 30° C. for 2 hours (dimethylformamide treatment). The cell-free extracts treated with dimethylformamide were dispensed in an amount of 50 µL into a 96-well plate (from AGC Techno Glass Co., Ltd.), followed by adding 50 µL of phosphate buffer (pH 6.5) containing 6 mM NADPH, and 100 µL of phosphate buffer (pH 6.5) containing 133 mM 2,3-butanedione. The mixture was reacted at 30° C. NADPH fluorescence was measured with time using an UV transilluminator and recording system FAS-III (from Toyobo Co., Ltd.). An enzyme solution in which the reaction did not proceed showed the remaining NADPH fluorescence, while a cell-free extract in which the reaction had proceeded showed reduced fluorescence with the decrease in NADPH. Enzymes which showed quenched fluorescence in a short time compared to the control cell-free extract of *E. coli* HB101 (pNKP) (wild-type enzyme) were selected as enzymes having high reactivity in the presence of dimethylformamide, i.e., altered carbonyl reductases having better stability to an organic solvent. Plasmids were extracted from the culture media of the selected enzymes, and the base sequence of the mutant RKP genes was determined using BigDye Terminator Cycle Sequencing Kit (from Applied Biosystems Japan, Ltd.) and Applied Biosystems 3130xl Genetic Analyzer (from Applied Biosystems Japan, Ltd.), whereby the mutation sites were identified. The obtained altered carbonyl reductases having better stability to an organic solvent are shown in Table 2.

TABLE 2

| Plasmid | Mutation site |
| --- | --- |
| pNKPm01 | T257S |
| pNKPm02 | K259E |
| pNKPm03 | S267P |
| pNKPm04 | K270M |
| pNKPm05 | N102I-E226G-S267P |
| pNKPm06 | H71R-G300D |

The six enzymes shown in Table 2 having better stability to an organic solvent were obtained.

(Example 3) Selection 2 of Altered Carbonyl Reductase

Altered carbonyl reductases having better stability to an organic solvent were selected from the mutant enzyme library 1. The recombinant bacteria in the mutant enzyme library 1 prepared in Example 1 and *E. coli* HB101 (pNKP) (control) prepared in Reference Example 3 were each inoculated on an LB medium plate containing 100 µg/mL ampicillin. The thus obtained colonies were transferred to a nylon membrane (Biodyne A, 0.45 µm) heated to 40° C. The nylon membrane was immersed in 50 mM 3-(N-morpholino)propanesulfonic acid (MOPS) buffer containing 30% dimethylformamide at 40° C. for 30 minutes. Then, the nylon membrane was immersed in 50 mM MOPS buffer containing 1 mM NADP$^+$, 200 µM nitroblue tetrazolium, 10 µM 1-methoxy-5-methylphenazinium methylsulfate, and 10% (v/v) 2-propanol at room temperature for 30 minutes. Thereafter, the nylon membrane was washed with distilled water, and then stained colonies were selected as candidates for recombinant bacteria with altered carbonyl reductases having better stability to dimethylformamide. The candidate strains were each inoculated into 5 ml of 2×YT medium (1.6% tryptone, 1.0% yeast extract, and 0.5% sodium chloride, pH 7.0) containing 200 µg/ml ampicillin, and cultured for 20 hours. The cells in the obtained culture media were collected by centrifugation and suspended in 100 mM phosphate buffer (pH 6.5) in an amount of ⅙ of the amount of the culture medium. The suspension was disrupted with a model UH-50 ultrasonic homogenizer (from SMT), followed by removing the cell debris by centrifugation to obtain a cell-free extract. To 20 µL of each of the cell-free extracts were added dimethylformamide at a final concentration of 20, 23, 26, or 30% and 50 mM MOPS buffer (pH 7.0) so that the total amount of the mixture was 40 µL, followed by heating at 40° C. for 30 minutes. After the mixture was cooled on ice for 1 minute, 200 µL of 50 mM MOPS buffer containing 1 mM NADP$^+$, 200 µM nitroblue tetrazolium, 10 µM 1-methoxy-5-methylphenazinium methylsulfate, and 10% (v/v) 2-propanol was added. Each reaction mixture was transferred to a 96-well plate (from AGC Techno Glass Co., Ltd.) and observed for 1 hour. Stained samples were selected as recombinant bacteria with altered carbonyl reductases having better stability to dimethylformamide. Plasmids were extracted from the culture media of the selected recombinant bacteria, and the base sequence of the mutant RKP genes was determined using BigDye Terminator Cycle Sequencing Kit (from Applied Biosystems Japan, Ltd.) and Applied Biosystems 3130xl Genetic Analyzer (from Applied Biosystems Japan, Ltd.), whereby the mutation sites were identified. The obtained altered carbonyl reductases having better stability to an organic solvent are shown in Table 3.

TABLE 3

| Plasmid | Mutation site |
|---|---|
| pNKPm01 | T257S |
| pNKPm02 | K259E |
| pNKPm03 | S267P |
| pNKPm04 | K270M |
| pNKPm05 | N102I-E226G-S267P |
| pNKPm06 | H71R-G300D |
| pNKPm07 | H71N-F195L |
| pNKPm08 | L177F-A220V |
| pNKPm09 | N45D-N175D-I183T |
| pNKPm10 | K22R |
| pNKPm11 | Y25F |
| pNKPm12 | T135A |
| pNKPm13 | Q155L |
| pNKPm14 | F195L |
| pNKPm15 | S212F |
| pNKPm16 | S212T |
| pNKPm17 | S212Y |
| pNKPm18 | E228V |
| pNKPm19 | N265K |
| pNKPm20 | R301C |
| pNKPm21 | S2I-V238I |
| pNKPm22 | E109G-K331F |
| pNKPm23 | I124L-S236N |
| pNKPm24 | I159F-K259E |
| pNKPm25 | L177F-A220V |
| pNKPm26 | K42R-Q155R-K279R |
| pNKPm28 | Q155L-S250P-Q298P |
| pNKPm29 | E56K-T138N-T190S-D254N |

The 29 enzymes shown in Table 3 having better stability to an organic solvent were obtained. Six enzymes out of these enzymes were the same mutant enzymes as those obtained in Example 2.

(Example 4) Evaluation 1 of Altered Carbonyl Reductase

The recombinant bacteria with the altered carbonyl reductases obtained in Example 2 and *E. coli* HB101 (pNKP) (control) prepared in Reference Example 3 were each cultured in the same manner as in Reference Example 4. The cells in the obtained culture media were collected by centrifugation and suspended in 100 mM phosphate buffer (pH 6.5) in an amount equal to to ⅕ of the amount of the culture medium. The suspension was disrupted with a model UH-50 ultrasonic homogenizer (from SMT), followed by removing the cell debris by centrifugation to obtain a cell-free extract. To 60 μL of each of the cell-free extracts was added 60 μL of phosphate buffer (pH 7.0) containing dimethylformamide at a final concentration of 30, 40, or 50%, followed by incubation at 30° C. (dimethylformamide treatment). The extracts treated with dimethylformamide after just 3 hours were sampled, diluted, and measured for activity for 2-pentanone reduction as described in Reference Example 4. The residual activity was calculated by the equation below and used as an indicator of stability to dimethylformamide.

Relative activity (%)=[enzyme activity after just 3 hours (with solvent)]/[enzyme activity after just 3 hours (without solvent)]×100

The relative activities of the wild-type enzyme and the altered carbonyl reductases evaluated in the presence of 40% dimethylformamide are shown in Table 4.

TABLE 4

| Mutation site | Residual activity (%) |
|---|---|
| Wild-type enzyme | 7.9 |
| T257S | 20.2 |
| K259E | 29.4 |
| N102I-E226G-S267P | 25.6 |
| K270M | 36.2 |
| H71R-G300D | 17.8 |

The altered carbonyl reductases shown in Table 4 had better stability to an organic solvent than the wild-type enzyme.

(Example 5) Evaluation 2 of Altered Carbonyl Reductase

The recombinant bacteria with the altered carbonyl reductases obtained in Example 3 and *E. coli* HB101 (pNKP) (control) prepared in Reference Example 3 were each cultured in the same manner as in Reference Example 4. The cells in the obtained culture media were collected by centrifugation and suspended in 100 mM phosphate buffer (pH 6.5) in an amount equal to to ⅕ of the amount of the culture medium. The suspension was disrupted with a model UH-50 ultrasonic homogenizer (from SMT), followed by removing the cell debris by centrifugation to obtain a cell-free extract. To 25 μL of each of the cell-free extracts was added the same amount of an 80% dimethylformamide solution, followed by leaving the mixture at 30° C. for 30 minutes. An amount of 200 μL of 100 mM phosphate buffer (pH 6.5) was added to the mixture and they were mixed. To 15 μL of the solution was added 250 μL of 100 mM phosphate buffer (pH 6.5) containing NADPH at a final concentration of 0.625 mM and 12.5 mM 2,3-butanedione dissolved therein, and they were mixed. After shaking for 5 seconds, NADPH absorbance (at 340 nm) was measured using a Benchmark Plus microplate spectrophotometer (from BIO-RAD) for 15 seconds. From the rate of decrease in the absorbance, the activity for 2,3-butanedione reduction was determined. The enzyme activity with the addition of dimethylformamide compared to the activity without dimethylformamide was calculated by the equation below and used as an indicator of stability to dimethylformamide.

Relative activity (%)=[enzyme activity (with dimethylformamide)]/[enzyme activity (without dimethylformamide)]×100

The relative activities of the wild-type enzyme and the altered carbonyl reductases are shown in Table 5.

TABLE 5

| Mutation site | Residual activity (%) |
|---|---|
| Wild-type enzyme | 8 |
| H71N-F195L | 24 |
| L177F-A220V | 47 |
| N45D-N175D-I183T | 16 |
| N102I-E226G-S267P | 26 |
| K22R | 13 |
| Y25F | 11 |
| T135A | 13 |
| Q155L | 13 |
| F195L | 29 |
| S212F | 11 |
| S212T | 10 |
| S212Y | 12 |
| E228V | 28 |

TABLE 5-continued

| Mutation site | Residual activity (%) |
|---|---|
| T257S | 20 |
| K259E | 29 |
| N265K | 28 |
| S267P | 38 |
| K270M | 38 |
| R301C | 41 |
| S2I-V238I | 36 |
| H71R-G300D | 12 |
| E109G-K331F | 9 |
| I124L-S236N | 38 |
| I159F-K259E | 15 |
| L177F-A220V | 47 |
| K42R-Q155R-K279R | 14 |
| N45D-N175D-I183T | 16 |
| Q155L-S250P-Q298P | 23 |
| E56K-T138N-T190S-D254N | 14 |

The altered carbonyl reductases shown in Table 5 had better stability to an organic solvent than the wild-type enzyme.

(Example 6) Preparation 1 of Altered Carbonyl Reductase with Multiple Mutations

A double-stranded DNA encoding an N-terminal polypeptide containing a T257S amino acid substitution relative to the amino acid sequence of SEQ ID NO:1 (N-terminal DNA) was obtained by PCR using the plasmid pNKPm02 obtained in Example 2 as a template, primer 1: 5'-GGGAATTCCATATGAGTGTTTTAGTTACAGG-3' (SEQ ID NO:4 in the sequence listing), and primer 3: 5'-GTTAATTTCATTAGCGCGATTTTTAATTACATG-3' (SEQ ID NO:6 in the sequence listing). Similarly, a double-stranded DNA encoding a C-terminal polypeptide containing H71R and K259E amino acid substitutions relative to the amino acid sequence of SEQ ID NO:1 (C-terminal DNA) was obtained by PCR using the plasmid pNKPm02 as a template, primer 4: 5'-CATGTAATTAAAAATCGCGCTAATGAAATTAAC-3' (SEQ ID NO:7 in the sequence listing), and primer 2: 5'-ATACGCGTCGACTTACTATTGTTCTTGAACCTTCA-3' (SEQ ID NO:5 in the sequence listing). The N-terminal DNA and the C-terminal DNA were mixed, and with the DNA mixture as a template, PCR was carried out using primer 1 and primer 2 to obtain a double-stranded DNA encoding a polypeptide containing H71R and K259E amino acid substitutions in the amino acid sequence of SEQ ID NO:1. The double-stranded DNA was introduced into pUCN18 in the same manner as in Reference Example 2 to prepare pNKPm30. E. coli HB101 competent cells (from Takara Bio, Inc.) were transformed with the pNKPm30, whereby a recombinant organism E. coli HB101 (pNKPm30) producing an altered carbonyl reductase H71R-K259E was obtained.

(Example 7) Preparation 2 of Altered Carbonyl Reductase with Multiple Mutations

A double-stranded DNA encoding an N-terminal polypeptide containing a T257S amino acid substitution relative to the amino acid sequence of SEQ ID NO:1 (N-terminal DNA) was obtained by PCR using the plasmid pNKPm02 obtained in Example 2 as a template, primer 1: 5'-GGGAATTCCATATGAGTGTTTTAGTTACAGG-3' (SEQ ID NO:4 in the sequence listing), and primer 5: 5'-GATCAAC-CTTTCACCGCTTAACTCATCATTATG-3' (SEQ ID NO:8 in the sequence listing). Similarly, a double-stranded DNA encoding a C-terminal polypeptide containing T257S and K259E amino acid substitutions relative to the amino acid sequence of SEQ ID NO:1 (C-terminal DNA) was obtained by PCR using the plasmid pNKPm02 as a template, primer 6: 5'-CATAATGATGAGTTAAGCGGTGAAAGGTTGATC-3' (SEQ ID NO:9 in the sequence listing), and primer 2: 5'-ATACGCGTCGACTTACTATTGTTCTTGAACCTTCA-3' (SEQ ID NO:5 in the sequence listing). The N-terminal DNA and the C-terminal DNA were mixed, and with the DNA mixture as a template, PCR was carried out using primer 1 and primer 2 to obtain a double-stranded DNA encoding a polypeptide containing T257S and K259E amino acid substitutions in the amino acid sequence of SEQ ID NO:1. The double-stranded DNA was introduced into pUCN18 in the same manner as in Reference Example 2 to prepare pNKPm31. E. coli HB101 competent cells (from Takara Bio, Inc.) were transformed with the pNKPm31, whereby a recombinant organism E. coli HB101 (pNKPm31) producing an altered carbonyl reductase T257S-K259E was obtained.

(Example 8) Preparation 3 of Altered Carbonyl Reductase with Multiple Mutations

A double-stranded DNA encoding an N-terminal polypeptide containing K259E and G300D amino acid substitutions relative to the amino acid sequence of SEQ ID NO:1 (N-terminal DNA) was obtained by PCR using the plasmid pNKPm02 obtained in Example 2 as a template, primer 1: 5'-GGGAATTCCATATGAGTGTTTTAGTTACAGG-3' (SEQ ID NO:4 in the sequence listing), and primer 7: 5'-CTCGTTATGGACACGATCTCCTTGAGGTAACTC-3' (SEQ ID NO:10 in the sequence listing). Similarly, a double-stranded DNA encoding a C-terminal polypeptide containing a G300D amino acid substitution relative to the amino acid sequence of SEQ ID NO:1 (C-terminal DNA) was obtained by PCR using the plasmid pNKPm02 as a template, primer 8: 5'-GAGTTACCTCAAGGAGATCGTGTCCATAACGAG-3' (SEQ ID NO:11 in the sequence listing), and primer 2: 5'-ATACGCGTCGACTTACTATTGTTCTTGAACCTTCA-3' (SEQ ID NO:5 in the sequence listing). The N-terminal DNA and the C-terminal DNA were mixed, and with the DNA mixture as a template, PCR was carried out using primer 1 and primer 2 to obtain a double-stranded DNA encoding a polypeptide containing K259E and G300D amino acid substitutions in the amino acid sequence of SEQ ID NO:1. The double-stranded DNA was introduced into pUCN18 in the same manner as in Reference Example 2 to prepare pNKPm32. E. coli HB101 competent cells (from Takara Bio, Inc.) were transformed with the pNKPm32, whereby a recombinant organism E. coli HB101 (pNKPm32) producing an altered carbonyl reductase K259E-G300D was obtained.

(Example 9) Preparation 4 of Altered Carbonyl Reductase with Multiple Mutations

A double-stranded DNA encoding an N-terminal polypeptide containing H71R and K270M amino acid substitutions relative to the amino acid sequence of SEQ ID NO:1 (N-terminal DNA) was obtained by PCR using the plasmid pNKPm04 obtained in Example 2 as a template, primer 1: 5'-GGGAATTCCATATGAGTGTTTTAGTTACAGG-3' (SEQ ID NO:4 in the sequence listing), and primer 9: 5'-GTTAATTTCATTAGCGCGATTTTTAATTACATG-3' (SEQ ID NO:12 in the sequence listing). Similarly, a double-stranded DNA encoding a C-terminal polypeptide containing H71R and K270M amino acid substitutions relative to the amino acid sequence of SEQ ID NO:1 (C-terminal DNA) was obtained by PCR using the plasmid pNKPm02 as a template, primer 10: 5'-CATGTAAT-TAAAAATCGCGCTAATGAAATTAAC-3' (SEQ ID NO:13 in the sequence listing), and primer 2: 5'-ATACGCGTCGACTTACTATTGTTCTTGAACCT-TCA-3' (SEQ ID NO:5 in the sequence listing). The N-terminal DNA and the C-terminal DNA were mixed, and with the DNA mixture as a template, PCR was carried out using primer 1 and primer 2 to obtain a double-stranded DNA encoding a polypeptide containing H71R and K270M amino acid substitutions in the amino acid sequence of SEQ ID NO:1. The double-stranded DNA was introduced into pUCN18 in the same manner as in Reference Example 2 to prepare pNKPm33. E. coli HB101 competent cells (from Takara Bio, Inc.) were transformed with the pNKPm33, whereby a recombinant organism E. coli HB101 (pNKPm33) producing an altered carbonyl reductase H71R-K270M was obtained.

(Example 10) Preparation 5 of Altered Carbonyl Reductase with Multiple Mutations A double-stranded DNA encoding an N-terminal polypeptide containing an N102I amino acid substitution relative to the amino acid sequence of SEQ ID NO:1 (N-terminal DNA) was obtained by PCR using the plasmid pNKPm04 obtained in Example 2 as a template, primer 1: 5'-GGGAAT-TCCATATGAGTGTTTTAGTTACAGG-3' (SEQ ID NO:4 in the sequence listing), and primer 11: 5'-GGATACCTT-TAGTACCAATAACAGCTGGGATTAAG-3' (SEQ ID NO:14 in the sequence listing). Similarly, a double-stranded DNA encoding a C-terminal polypeptide containing N102I and K270M amino acid substitutions relative to the amino acid sequence of SEQ ID NO:1 (C-terminal DNA) was obtained by PCR using the plasmid pNKPm04 as a template, primer 12: 5'-CTTAATCCCAGCTGTTATTGG-TACTAAAGGTATCC-3' (SEQ ID NO:15 in the sequence listing), and primer 2: 5'-ATACGCGTCGACTTACTATT-GTTCTTGAACCTTCA-3' (SEQ ID NO:5 in the sequence listing). The N-terminal DNA and the C-terminal DNA were mixed, and with the DNA mixture as a template, PCR was carried out using primer 1 and primer 2 to obtain a double-stranded DNA encoding a polypeptide containing N102I and K270M amino acid substitutions in the amino acid sequence of SEQ ID NO:1. The double-stranded DNA was introduced into pUCN18 in the same manner as in Reference Example 2 to prepare pNKPm34. E. coli HB101 competent cells (from Takara Bio, Inc.) were transformed with the pNKPm34, whereby a recombinant organism E. coli HB101 (pNKPm34) producing an altered carbonyl reductase N102I-K270M was obtained.

(Example 11) Preparation 6 of Altered Carbonyl Reductase with Multiple Mutations A double-stranded DNA encoding an N-terminal polypeptide containing an E226G amino acid substitution relative to the amino acid sequence of SEQ ID NO:1 (N-terminal DNA) was obtained by PCR using the plasmid pNKPm04 obtained in Example 2 as a template, primer 1: 5'-GGGAATTCCATATGAGTGTTTTAGTTACAGG-3' (SEQ ID NO:4 in the sequence listing), and primer 13: 5'-TTTATCAATTTCACTGCCTGTTGGAG-CAAACATAGC-3' (SEQ ID NO:16 in the sequence listing).

Similarly, a double-stranded DNA encoding a C-terminal polypeptide containing an NE226G amino acid substitution relative to the amino acid sequence of SEQ ID NO:1 (C-terminal DNA) was obtained by PCR using the plasmid pNKPm04 as a template, primer 14: 5'-GCTATGTTT-GCTCCAACAGGCAGTGAAATTGATAAA-3' (SEQ ID NO:17 in the sequence listing), and primer 2: 5'-ATACGCGTCGACTTACTATTGTTCTTGAACCT-TCA-3' (SEQ ID NO:5 in the sequence listing). The N-terminal DNA and the C-terminal DNA were mixed, and with the DNA mixture as a template, PCR was carried out using primer 1 and primer 2 to obtain a double-stranded DNA encoding a polypeptide containing E226G and K270M amino acid substitutions in the amino acid sequence of SEQ ID NO:1. The double-stranded DNA was introduced into pUCN18 in the same manner as in Reference Example 2 to prepare pNKPm35. E. coli HB101 competent cells (from Takara Bio, Inc.) were transformed with the pNKPm35, whereby a recombinant organism E. coli HB101 (pNKPm35) producing an altered carbonyl reductase E226G-K270M was obtained.

(Example 12) Preparation 7 of Altered Carbonyl Reductase with Multiple Mutations A double-stranded DNA encoding an N-terminal polypeptide containing a T257S amino acid substitution relative to the amino acid sequence of SEQ ID NO:1 (N-terminal DNA) was obtained by PCR using the plasmid pNKPm04 obtained in Example 2 as a template, primer 1: 5'-GGGAAT-TCCATATGAGTGTTTTAGTTACAGG-3' (SEQ ID NO:4 in the sequence listing), and primer 15: 5'-GATCAAC-CTTTTACCGCTTAACTCATCATTATG-3' (SEQ ID NO:18 in the sequence listing). Similarly, a double-stranded DNA encoding a C-terminal polypeptide containing T257S and K270M amino acid substitutions relative to the amino acid sequence of SEQ ID NO:1 (C-terminal DNA) was obtained by PCR using the plasmid pNKPm04 as a template, primer 16: 5'-CATAATGATGAGTTAAGCGG-TAAAAGGTTGATC-3' (SEQ ID NO:19 in the sequence listing), and primer 2: 5'-ATACGCGTCGACTTACTATT-GTTCTTGAACCTTCA-3' (SEQ ID NO:5 in the sequence listing). The N-terminal DNA and the C-terminal DNA were mixed, and with the DNA mixture as a template, PCR was carried out using primer 1 and primer 2 to obtain a double-stranded DNA encoding a polypeptide containing T257S and K270M amino acid substitutions in the amino acid sequence of SEQ ID NO:1. The double-stranded DNA was introduced into pUCN18 in the same manner as in Reference Example 2 to prepare pNKPm36. E. coli HB101 competent cells (from Takara Bio, Inc.) were transformed with the pNKPm36, whereby a recombinant organism E. coli HB101 (pNKPm36) producing an altered carbonyl reductase T257S-K270M was obtained.

(Example 13) Preparation 8 of Altered Carbonyl Reductase with Multiple Mutations A double-stranded DNA encoding an N-terminal polypeptide containing a K259E amino acid substitution relative to the amino acid sequence of SEQ ID NO:1 (N-terminal DNA) was obtained by PCR using the plasmid pNKPm04 obtained in Example 2 as a template, primer 1: 5'-GGGAAT-TCCATATGAGTGTTTTAGTTACAGG-3' (SEQ ID NO:4 in the sequence listing), and primer 17: 5'-GACAAGAT-CAACCTTTCACCAGTTAACTCATC-3' (SEQ ID NO:20 in the sequence listing). Similarly, a double-stranded DNA encoding a C-terminal polypeptide containing K259E and K270M amino acid substitutions relative to the amino acid sequence of SEQ ID NO:1 (C-terminal DNA) was obtained by PCR using the plasmid pNKPm04 as a template, primer 18: 5'-GATGAGTTAACTGGTGAAAGGTTGATCTT-GTC-3' (SEQ ID NO:21 in the sequence listing), and primer 2: 5'-ATACGCGTCGACTTACTATTGTTCTTGAACCT-TCA-3' (SEQ ID NO:5 in the sequence listing). The N-terminal DNA and the C-terminal DNA were mixed, and with the DNA mixture as a template, PCR was carried out using primer 1 and primer 2 to obtain a double-stranded DNA encoding a polypeptide containing K259E and K270M amino acid substitutions in the amino acid sequence of SEQ ID NO:1. The double-stranded DNA was introduced into pUCN18 in the same manner as in Reference Example 2 to prepare pNKPm37. E. coli HB101 competent cells (from Takara Bio, Inc.) were transformed with the pNKPm37, whereby a recombinant organism E. coli HB101 (pNKPm37) producing an altered carbonyl reductase K259E-K270M was obtained.

(Example 14) Preparation 9 of Altered Carbonyl Reductase with Multiple Mutations A double-stranded DNA encoding an N-terminal polypeptide containing an S267P amino acid substitution relative to the amino acid sequence of SEQ ID NO:1 (N-terminal DNA) was obtained by PCR using the plasmid pNKPm04 obtained in Example 2 as a template, primer 1: 5'-GGGAAT-TCCATATGAGTGTTTTAGTTACAGG-3' (SEQ ID NO:4 in the sequence listing), and primer 19: 5'-TTTGCATAGT-GAACGGAGCATTTGACAAG-3' (SEQ ID NO:22 in the sequence listing). Similarly, a double-stranded DNA encoding a C-terminal polypeptide containing S267P and K270M amino acid substitutions relative to the amino acid sequence of SEQ ID NO:1 (C-terminal DNA) was obtained by PCR using the plasmid pNKPm04 as a template, primer 20: 5'-CTTGTCAAATGCTCCGTTCACTATGCAAA-3' (SEQ ID NO:23 in the sequence listing), and primer 2: 5'-ATACGCGTCGACTTACTATTGTTCTTGAACCT-TCA-3' (SEQ ID NO:5 in the sequence listing). The N-terminal DNA and the C-terminal DNA were mixed, and with the DNA mixture as a template, PCR was carried out using primer 1 and primer 2 to obtain a double-stranded DNA encoding a polypeptide containing S267P and K270M amino acid substitutions in the amino acid sequence of SEQ ID NO:1. The double-stranded DNA was introduced into pUCN18 in the same manner as in Reference Example 2 to prepare pNKPm38. E. coli HB101 competent cells (from Takara Bio, Inc.) were transformed with the pNKPm38, whereby a recombinant organism E. coli HB101 (pNKPm38) producing an altered carbonyl reductase S267P-K270M was obtained.

(Example 15) Preparation 10 of Altered Carbonyl Reductase with Multiple Mutations A double-stranded DNA encoding an N-terminal polypeptide containing K270M and G300D amino acid substitutions relative to the amino acid sequence of SEQ ID NO:1 (N-terminal DNA) was obtained by PCR using the plasmid pNKPm04 obtained in Example 2 as a template, primer 1: 5'-GGGAATTCCATATGAGTGTTTTAGTTACAGG-3' (SEQ ID NO:4 in the sequence listing), and primer 21: 5'-CTCGTTATGGACACGATCTCCTTGAGGTAACTC-3' (SEQ ID NO:24 in the sequence listing). Similarly, a double-stranded DNA encoding a C-terminal polypeptide containing a G300D amino acid substitution relative to the amino acid sequence of SEQ ID NO:1 (C-terminal DNA) was obtained by PCR using the plasmid pNKPm04 as a template, primer 22: 5'-GAGTTACCTCAAGGAGATCGTGTC-CATAACGAG-3' (SEQ ID NO:25 in the sequence listing), and primer 2: 5'-ATACGCGTCGACTTACTATTGTTCTT-GAACCTTCA-3' (SEQ ID NO:5 in the sequence listing). The N-terminal DNA and the C-terminal DNA were mixed, and with the DNA mixture as a template, PCR was carried out using primer 1 and primer 2 to obtain a double-stranded DNA encoding a polypeptide containing K270M and G300D amino acid substitutions in the amino acid sequence of SEQ ID NO:1. The double-stranded DNA was introduced into pUCN18 in the same manner as in Reference Example 2 to prepare pNKPm39. E. coli HB101 competent cells (from Takara Bio, Inc.) were transformed with the pNKPm39, whereby a recombinant organism E. coli HB101 (pNKPm39) producing an altered carbonyl reductase K270M-G300D was obtained.

(Example 16) Evaluation 1 of Altered Carbonyl Reductase with Multiple Mutations

The recombinant bacteria with the respective altered carbonyl reductases with multiple mutations obtained in Examples 6 to 15 and E. coli HB101 (pNKP) (control) prepared in Reference Example 3 were each cultured in the same manner as in Reference Example 4. The stability of each altered carbonyl reductase with multiple mutations to dimethylformamide was evaluated in the same manner as in Example 4. The relative activities of the wild-type enzyme and the altered carbonyl reductases evaluated in the presence of 40% dimethylformamide are shown in Table 6.

TABLE 6

| Mutation site | Residual activity (%) |
|---|---|
| Wilde-type enzyme | 8 |
| K259E | 25 |
| K270M | 31 |
| H71S-K259E | 30 |
| T257S-K259E | 38 |
| K259E-G300D | 36 |
| H71R-K270M | 29 |
| N102I-K270M | 26 |
| E226G-K270M | 31 |
| T257S-K270M | 44 |
| K259E-K270M | 64 |
| S267P-K270M | 33 |
| K270M-G300D | 44 |

The altered carbonyl reductases shown in Table 6 had better stability to an organic solvent than the wild-type enzyme.

(Example 17) Preparation 11 of Altered Carbonyl Reductase with Multiple Mutations A double-stranded DNA encoding an N-terminal polypeptide containing an S2I amino acid substitution relative to the amino acid sequence of SEQ ID NO:1 (N-terminal DNA) was obtained by PCR using the plasmid pNKPm37 obtained in Example 7 as a template, primer 1: 5'-GGGAAT-TCCATATGAGTGTTTTAGTTACAGG-3' (SEQ ID NO:4 in the sequence listing), and primer 23: 5'-CCAGTAGCAC-CTGTAACTAAAACAATCAT-3' (SEQ ID NO:26 in the sequence listing). Similarly, a double-stranded DNA encoding a C-terminal polypeptide containing S2I, K259E, and K270M amino acid substitutions relative to the amino acid sequence of SEQ ID NO:1 (C-terminal DNA) was obtained by PCR using the plasmid pNKPm37 as a template, primer 24: 5'-ATGATTGTTTTAGTTACAGGTGCTACTGG-3' (SEQ ID NO:27 in the sequence listing), and primer 2: 5'-ATACGCGTCGACTTACTATTGTTCTTGAACCT-TCA-3' (SEQ ID NO:5 in the sequence listing). The N-terminal DNA and the C-terminal DNA were mixed, and with the DNA mixture as a template, PCR was carried out using primer 1 and primer 2 to obtain a double-stranded DNA encoding a polypeptide containing S2I, K259E, and K270M amino acid substitutions in the amino acid sequence of SEQ ID NO:1. The double-stranded DNA was introduced into pUCN18 in the same manner as in Reference Example 2 to prepare pNKPm40. E. coli HB101 competent cells (from Takara Bio, Inc.) were transformed with the pNKPm40, whereby a recombinant organism E. coli HB101 (pNKPm40) producing an altered carbonyl reductase S2I-K259E-K270M was obtained.

(Example 18) Preparation 12 of Altered Carbonyl Reductase with Multiple Mutations A double-stranded DNA encoding an N-terminal polypeptide containing an I124L amino acid substitution relative to the amino acid sequence of SEQ ID NO:1 (N-terminal DNA) was obtained by PCR using the plasmid pNKPm37 obtained in Example 7 as a template, primer 1: 5'-GGGAAT-TCCATATGAGTGTTTTAGTTACAGG-3' (SEQ ID NO:4 in the sequence listing), and primer 25: 5'-GGCAGCAAT-TGAAGAAGTCAGAACAAATTTCTTCAC-3' (SEQ ID NO:28 in the sequence listing). Similarly, a double-stranded DNA encoding a C-terminal polypeptide containing I124L, K259E, and K270M amino acid substitutions relative to the amino acid sequence of SEQ ID NO:1 (C-terminal DNA) was obtained by PCR using the plasmid pNKPm37 as a template, primer 26: 5'-GTGAAGAAATTTGTTCTGACT-TCTTCAATTGCTGCC-3' (SEQ ID NO:29 in the sequence listing), and primer 2: 5'-ATACGCGTCGACTTACTATT-GTTCTTGAACCTTCA-3' (SEQ ID NO:5 in the sequence listing). The N-terminal DNA and the C-terminal DNA were mixed, and with the DNA mixture as a template, PCR was carried out using primer 1 and primer 2 to obtain a double-stranded DNA encoding a polypeptide containing I124L, K259E, and K270M amino acid substitutions in the amino acid sequence of SEQ ID NO:1. The double-stranded DNA was introduced into pUCN18 in the same manner as in Reference Example 2 to prepare pNKPm41. E. coli HB101 competent cells (from Takara Bio, Inc.) were transformed with the pNKPm41, whereby a recombinant organism E. coli HB101 (pNKPm41) producing an altered carbonyl reductase I124L-K259E-K270M was obtained.

(Example 19) Preparation 13 of Altered Carbonyl Reductase with Multiple Mutations A double-stranded DNA encoding an N-terminal polypeptide containing an L177F amino acid substitution relative to the amino acid sequence of SEQ ID NO:1 (N-terminal DNA) was obtained by PCR using the plasmid pNKPm37 obtained in Example 7 as a template, primer 1: 5'-GGGAAT-TCCATATGAGTGTTTTAGTTACAGG-3' (SEQ ID NO:4 in the sequence listing), and primer 27: 5'-CCTTTAT-TCTCTTCAAAGAAGTTCCAAGCAGC-3' (SEQ ID NO:30 in the sequence listing). Similarly, a double-stranded DNA encoding a C-terminal polypeptide containing L177F, K259E, and K270M amino acid substitutions relative to the amino acid sequence of SEQ ID NO:1 (C-terminal DNA) was obtained by PCR using the plasmid pNKPm37 as a template, primer 28: 5'-GCTGCTTGGAACTTCTTT-GAAGAGAATAAAGG-3' (SEQ ID NO:31 in the sequence listing), and primer 2: 5'-ATACGCGTCGACTTACTATT-GTTCTTGAACCTTCA-3' (SEQ ID NO:5 in the sequence listing). The N-terminal DNA and the C-terminal DNA were mixed, and with the DNA mixture as a template, PCR was carried out using primer 1 and primer 2 to obtain a double-stranded DNA encoding a polypeptide containing L177F, K259E, and K270M amino acid substitutions in the amino acid sequence of SEQ ID NO:1. The double-stranded DNA was introduced into pUCN18 in the same manner as in Reference Example 2 to prepare pNKPm42. E. coli HB101 competent cells (from Takara Bio, Inc.) were transformed with the pNKPm42, whereby a recombinant organism E. coli HB101 (pNKPm42) producing an altered carbonyl reductase L177F-K259E-K270M was obtained.

(Example 20) Preparation 14 of Altered Carbonyl Reductase with Multiple Mutations A double-stranded DNA encoding an N-terminal polypeptide containing an F195L amino acid substitution relative to the amino acid sequence of SEQ ID NO:1 (N-terminal DNA) was obtained by PCR using the plasmid pNKPm37 obtained in Example 7 as a template, primer 1: 5'-GGGAAT-TCCATATGAGTGTTTTAGTTACAGG-3' (SEQ ID NO:4 in the sequence listing), and primer 29: 5'-GGAC-CAAAGACCAGAACTGGGTTGATCG-3' (SEQ ID NO:32 in the sequence listing). Similarly, a double-stranded DNA encoding a C-terminal polypeptide containing F195L, K259E, and K270M amino acid substitutions relative to the amino acid sequence of SEQ ID NO:1 (C-terminal DNA) was obtained by PCR using the plasmid pNKPm37 as a template, primer 30: 5'-CGATCAACCCAGTTCTG-GTCTTTGGTCC-3' (SEQ ID NO:33 in the sequence listing), and primer 2: 5'-ATACGCGTCGACTTACTATTGT-TCTTGAACCTTCA-3' (SEQ ID NO:5 in the sequence listing). The N-terminal DNA and the C-terminal DNA were mixed, and with the DNA mixture as a template, PCR was carried out using primer 1 and primer 2 to obtain a double-stranded DNA encoding a polypeptide containing F195L, K259E, and K270M amino acid substitutions in the amino acid sequence of SEQ ID NO:1. The double-stranded DNA was introduced into pUCN18 in the same manner as in Reference Example 2 to prepare pNKPm43. E. coli HB101 competent cells (from Takara Bio, Inc.) were transformed with the pNKPm43, whereby a recombinant organism E. coli HB101 (pNKPm43) producing an altered carbonyl reductase F195L-K259E-K270M was obtained.

(Example 21) Preparation 15 of Altered Carbonyl Reductase with Multiple Mutations A double-stranded DNA encoding an N-terminal polypeptide containing an A220V amino acid substitution relative to the amino acid sequence of SEQ ID NO:1 (N-terminal DNA) was obtained by PCR using the plasmid pNKPm37 obtained in Example 7 as a template, primer 1: 5'-GGGAATTCCATATGAGTGTTTTAGTTACAGG-3' (SEQ ID NO:4 in the sequence listing), and primer 31: 5'-CTGTTGGAGCAAACATCACTTCCTTGATGATTTC-3' (SEQ ID NO:34 in the sequence listing). Similarly, a double-stranded DNA encoding a C-terminal polypeptide containing A220, K259E, and K270M amino acid substitutions relative to the amino acid sequence of SEQ ID NO:1

(C-terminal DNA) was obtained by PCR using the plasmid pNKPm37 as a template, primer 32: 5'-GAAATCAT-CAAGGAAGTGATGTTTGCTCCAACAG-3' (SEQ ID NO:35 in the sequence listing), and primer 2: 5'-ATACGCGTCGACTTACTATTGTTCTTGAACCT-TCA-3' (SEQ ID NO:5 in the sequence listing). The N-terminal DNA and the C-terminal DNA were mixed, and with the DNA mixture as a template, PCR was carried out using primer 1 and primer 2 to obtain a double-stranded DNA encoding a polypeptide containing A220V, K259E, and K270M amino acid substitutions in the amino acid sequence of SEQ ID NO:1. The double-stranded DNA was introduced into pUCN18 in the same manner as in Reference Example 2 to prepare pNKPm44. *E. coli* HB101 competent cells (from Takara Bio, Inc.) were transformed with the pNKPm44, whereby a recombinant organism *E. coli* HB101 (pNKPm44) producing an altered carbonyl reductase A220V-K259E-K270M was obtained.

(Example 22) Preparation 16 of Altered Carbonyl Reductase with Multiple Mutations A double-stranded DNA encoding an N-terminal polypeptide containing an S236N amino acid substitution relative to the amino acid sequence of SEQ ID NO:1 (N-terminal DNA) was obtained by PCR using the plasmid pNKPm37 obtained in Example 7 as a template, primer 1: 5'-GGGAATTCCATATGAGTGTTTTAGTTACAGG-3' (SEQ ID NO:4 in the sequence listing), and primer 33: 5'-CGTACATCAACATAGTTACCAAAAACAGATT-TATC-3' (SEQ ID NO:36 in the sequence listing). Similarly, a double-stranded DNA encoding a C-terminal polypeptide containing S236N, K259E, and K270M amino acid substitutions relative to the amino acid sequence of SEQ ID NO:1 (C-terminal DNA) was obtained by PCR using the plasmid pNKPm37 as a template, primer 34: 5'-GATAAATCT-GTTTTTGGTAACTATGTTGATGTACG-3' (SEQ ID NO:37 in the sequence listing), and primer 2: 5'-ATACGCGTCGACTTACTATTGTTCTTGAACCT-TCA-3' (SEQ ID NO: 5 in the sequence listing). The N-terminal DNA and the C-terminal DNA were mixed, and with the DNA mixture as a template, PCR was carried out using primer 1 and primer 2 to obtain a double-stranded DNA encoding a polypeptide containing S236N, K259E, and K270M amino acid substitutions in the amino acid sequence of SEQ ID NO:1. The double-stranded DNA was introduced into pUCN18 in the same manner as in Reference Example 2 to prepare pNKPm45. *E. coli* HB101 competent cells (from Takara Bio, Inc.) were transformed with the pNKPm45, whereby a recombinant organism *E. coli* HB101 (pNKPm45) producing an altered carbonyl reductase S236N-K259E-K270M was obtained.

(Example 23) Preparation 17 of Altered Carbonyl Reductase with Multiple Mutations A double-stranded DNA encoding an N-terminal polypeptide containing a V238I amino acid substitution relative to the amino acid sequence of SEQ ID NO:1 (N-terminal DNA) was obtained by PCR using the plasmid pNKPm37 obtained in Example 7 as a template, primer 1: 5'-GGGAAT-TCCATATGAGTGTTTTAGTTACAGG-3' (SEQ ID NO:4 in the sequence listing), and primer 35: 5'-GCTACAT-CACGTACATCAATATAACTACCAAAAAC-3' (SEQ ID NO:38 in the sequence listing). Similarly, a double-stranded DNA encoding a C-terminal polypeptide containing V238I, K259E, and K270M amino acid substitutions relative to the amino acid sequence of SEQ ID NO:1 (C-terminal DNA) was obtained by PCR using the plasmid pNKPm37 as a template, primer 36: 5'-GTTTTTGGTAGTTATATTGATG-TACGTGATGTAGC-3' (SEQ ID NO:39 in the sequence listing), and primer 2: 5'-ATACGCGTCGACTTACTATT-GTTCTTGAACCTTCA-3' (SEQ ID NO:5 in the sequence listing). The N-terminal DNA and the C-terminal DNA were mixed, and with the DNA mixture as a template, PCR was carried out using primer 1 and primer 2 to obtain a double-stranded DNA encoding a polypeptide containing V238I, K259E, and K270M amino acid substitutions in the amino acid sequence of SEQ ID NO:1. The double-stranded DNA was introduced into pUCN18 in the same manner as in Reference Example 2 to prepare pNKPm46. *E. coli* HB101 competent cells (from Takara Bio, Inc.) were transformed with the pNKPm46, whereby a recombinant organism *E. coli* HB101 (pNKPm46) producing an altered carbonyl reductase V238I-K259E-K270M was obtained.

(Example 24) Preparation 18 of Altered Carbonyl Reductase with Multiple Mutations A double-stranded DNA encoding an N-terminal polypeptide containing a T257S amino acid substitution relative to the amino acid sequence of SEQ ID NO:1 (N-terminal DNA) was obtained by PCR using the plasmid pNKPm37 obtained in Example 7 as a template, primer 1: 5'-GGGAAT-TCCATATGAGTGTTTTAGTTACAGG-3' (SEQ ID NO:4 in the sequence listing), and primer 37: 5'-GATCAAC-CTTTTACCGCTTAACTCATCATTATG-3' (SEQ ID NO:40 in the sequence listing). Similarly, a double-stranded DNA encoding a C-terminal polypeptide containing T257S, K259E, and K270M amino acid substitutions relative to the amino acid sequence of SEQ ID NO:1 (C-terminal DNA) was obtained by PCR using the plasmid pNKPm37 as a template, primer 38: 5'-CATAATGATGAGTTAAGCGG-TAAAAGGTTGATC-3' (SEQ ID NO:41 in the sequence listing), and primer 2: 5'-ATACGCGTCGACTTACTATT-GTTCTTGAACCTTCA-3' (SEQ ID NO:5 in the sequence listing). The N-terminal DNA and the C-terminal DNA were mixed, and with the DNA mixture as a template, PCR was carried out using primer 1 and primer 2 to obtain a double-stranded DNA encoding a polypeptide containing T257S, K259E, and K270M amino acid substitutions in the amino acid sequence of SEQ ID NO:1. The double-stranded DNA was introduced into pUCN18 in the same manner as in Reference Example 2 to prepare pNKPm47. *E. coli* HB101 competent cells (from Takara Bio, Inc.) were transformed with the pNKPm47, whereby a recombinant organism *E. coli* HB101 (pNKPm47) producing an altered carbonyl reductase T257S-K259E-K270M was obtained.

(Example 25) Preparation 19 of Altered Carbonyl Reductase with Multiple Mutations A double-stranded DNA encoding an N-terminal polypeptide containing K259E and N265K amino acid substitutions relative to the amino acid sequence of SEQ ID NO:1 (N-terminal DNA) was obtained by PCR using the plasmid pNKPm37 obtained in Example 7 as a template, primer 1: 5'-GGGAATTCCATATGAGTGTTTTAGTTACAGG-3' (SEQ ID NO: 4 in the sequence listing), and primer 39: 5'-GCATAGTGAATGAAGCTTTTGACAAGATCAAC-CTTTCACC-3' (SEQ ID NO:42 in the sequence listing). Similarly, a double-stranded DNA encoding a C-terminal polypeptide containing K259E, N265K, and K270M amino acid substitutions relative to the amino acid sequence of SEQ ID NO:1 (C-terminal DNA) was obtained by PCR using the plasmid pNKPm37 as a template, primer 40: 5'-GGTGAAAGGTTGATCTTGTCAAAAGCTTCAT-TCACTATGC-3' (SEQ ID NO:43 in the sequence listing), and primer 2: 5'-ATACGCGTCGACTTACTATTGTTCTT-GAACCTTCA-3' (SEQ ID NO:5 in the sequence listing). The N-terminal DNA and the C-terminal DNA were mixed, and with the DNA mixture as a template, PCR was carried out using primer 1 and primer 2 to obtain a double-stranded DNA encoding a polypeptide containing K259E, N265K, and K270M amino acid substitutions in the amino acid sequence of SEQ ID NO:1. The double-stranded DNA was introduced into pUCN18 in the same manner as in Reference Example 2 to prepare pNKPm48. *E. coli* HB101 competent cells (from Takara Bio, Inc.) were transformed with the pNKPm48, whereby a recombinant organism *E. coli* HB101 (pNKPm48) producing an altered carbonyl reductase K259E-N265K-K270M was obtained.

(Example 26) Preparation 20 of Altered Carbonyl Reductase with Multiple Mutations A double-stranded DNA encoding an N-terminal polypeptide containing K259E, K270M, and G300D amino acid substitutions relative to the amino acid sequence of SEQ ID NO:1 (N-terminal DNA) was obtained by PCR using the plasmid pNKPm37 obtained in Example 7 as a template, primer 1: 5'-GGGAATTCCATATGAGTGTTTTAGTTA-CAGG-3' (SEQ ID NO:4 in the sequence listing), and primer 41: 5'-CTCGTTATGGACACGATCTCCTTGAGG-TAACTC-3' (SEQ ID NO:44 in the sequence listing). Similarly, a double-stranded DNA encoding a C-terminal polypeptide containing K259E, K270M, and G300D amino acid substitutions relative to the amino acid sequence of SEQ ID NO:1 (C-terminal DNA) was obtained by PCR using the plasmid pNKPm37 as a template, primer 42: 5'-GAGTTAC-CTCAAGGAGATCGTGTCCATAACGAG-3' (SEQ ID NO:45 in the sequence listing), and primer 2: 5'-ATACGCGTCGACTTACTATTGTTCTTGAACCT-TCA-3' (SEQ ID NO:5 in the sequence listing). The N-terminal DNA and the C-terminal DNA were mixed, and with the DNA mixture as a template, PCR was carried out using primer 1 and primer 2 to obtain a double-stranded DNA encoding a polypeptide containing K259E, K270M, and G300D amino acid substitutions in the amino acid sequence of SEQ ID NO:1. The double-stranded DNA was introduced into pUCN18 in the same manner as in Reference Example 2 to prepare pNKPm49. *E. coli* HB101 competent cells (from Takara Bio, Inc.) were transformed with the pNKPm49, whereby a recombinant organism *E. coli* HB101 (pNKPm49) producing an altered carbonyl reductase K259E-K270M-G300D was obtained.

(Example 27) Preparation 21 of Altered Carbonyl Reductase with Multiple Mutations A double-stranded DNA encoding an N-terminal polypeptide containing K259E, K270M, and R301C amino acid substitutions relative to the amino acid sequence of SEQ ID NO:1 (N-terminal DNA) was obtained by PCR using the plasmid pNKPm37 obtained in Example 7 as a template, primer 1: 5'-GGGAATTCCATATGAGTGTTTTAGTTA-CAGG-3' (SEQ ID NO:4 in the sequence listing), and primer 43: 5'-CTTCTCGTTATGGACGCAACCTCCTTGAGG-TAACTCG-3' (SEQ ID NO:46 in the sequence listing). Similarly, a double-stranded DNA encoding a C-terminal polypeptide containing K259E, K270M, and R301C amino acid substitutions relative to the amino acid sequence of SEQ ID NO:1 (C-terminal DNA) was obtained by PCR using the plasmid pNKPm37 as a template, primer 44: 5'-CGAGTTACCTCAAGGAGGTTGCGTCCATAACGA-GAAG-3' (SEQ ID NO:47 in the sequence listing), and primer 2: 5'-ATACGCGTCGACTTACTATTGTTCTT-GAACCTTCA-3' (SEQ ID NO:5 in the sequence listing). The N-terminal DNA and the C-terminal DNA were mixed, and with the DNA mixture as a template, PCR was carried out using primer 1 and primer 2 to obtain a double-stranded DNA encoding a polypeptide containing K259E, K270M, and R301C amino acid substitutions in the amino acid sequence of SEQ ID NO:1. The double-stranded DNA was introduced into pUCN18 in the same manner as in Reference Example 2 to prepare pNKPm50. *E. coli* HB101 competent cells (from Takara Bio, Inc.) were transformed with the pNKPm50, whereby a recombinant organism *E. coli* HB101 (pNKPm50) producing an altered carbonyl reductase K259E-K270M-R301C was obtained.

(Example 28) Evaluation 2 of Altered Carbonyl Reductase with Multiple Mutations

The recombinant bacteria with the respective altered carbonyl reductases with multiple mutations obtained in Examples 17 to 27 and *E. coli* HB101 (pNKP) (control) prepared in Reference Example 3 were each cultured in the same manner as in Reference Example 4. The stability of each altered carbonyl reductase with multiple mutations to dimethylformamide was evaluated in the same manner as in Example 4. The relative activities of the wild-type enzyme and the altered carbonyl reductases evaluated in the presence of 50% dimethylformamide are shown in Table 7.

TABLE 7

| Mutation site | Residual activity (%) |
|---|---|
| Wild-type enzyme | 0 |
| K270M | 1 |
| K259E-K270M | 5 |
| S2I-K259E-K270M | 2 |
| I124L-K259E-K270M | 25 |
| L177F-K259E-K270M | 3 |
| F195L-K259E-K270M | 21 |
| A220V-K259E-K270M | 16 |
| S236N-K259E-K270M | 24 |
| V238I-K259E-K270M | 15 |
| T257S-K259E-K270M | 33 |
| N265K-K259E-K270M | 15 |
| G300D-K259E-K270M | 20 |
| R301C-K259E-K270M | 35 |

The altered carbonyl reductases shown in Table 7 had better stability to an organic solvent than the wild-type enzyme.

(Example 29) Preparation 2 of Mutant Enzyme Library

A mutant enzyme library was prepared in the same manner as in Example 1, using as a template the plasmid pNKPm37 containing the mutant RKP gene for K259E-K270M mutant enzyme obtained in Example 15. This library is referred to as mutant enzyme library 2.

(Example 30) Selection 3 of Altered Carbonyl Reductase

Altered carbonyl reductases having better resistance to the reaction inhibition by dimethylformamide, which is an organic solvent, were selected from the mutant enzyme library 2. The recombinant bacteria from the mutant enzyme library 2 prepared in Example 29 and *E. coli* HB101 (pNKP) (control) prepared in Reference Example 3 were each inoculated on an LB medium plate containing 100 μg/mL ampicillin.

The thus obtained colonies were transferred to a nylon membrane (Biodyne A, 0.45 μm), and the nylon membrane was immersed in 50 mM 3-(N-morpholino)propanesulfonic acid (MOPS) buffer containing 40% dimethylformamide for 30 to 60 minutes. Then, the nylon membrane was immersed in 50 mM MOPS buffer containing 1 mM NADP$^+$, 200 μM nitroblue tetrazolium, 10 μM 1-methoxy-5-methylphenazinium methylsulfate, and 5% (v/v) 2-propanol at room temperature for 30 minutes. Thereafter, the nylon membrane was washed with distilled water, and then stained colonies were selected as candidates for recombinant bacteria with altered carbonyl reductases having better resistance to the reaction inhibition by an organic solvent. The candidate strains were each inoculated into 5 ml of 2×YT medium (1.6% tryptone, 1.0% yeast extract, and 0.5% sodium chloride, pH 7.0) containing 200 μg/ml ampicillin, and cultured for 20 hours. The cells in the obtained culture media were disrupted and centrifuged, followed by removing the precipitate to obtain a cell-free extract. The cell-free extracts were dispensed in an amount of 200 μL into a 96-well plate (from AGC Techno Glass Co., Ltd.), followed by adding and mixing 50 μL of 0.1M phosphate buffer (pH 6.5) containing 0.625 mM NADPH and 10 mM 2,3-butanedione. NADPH fluorescence was measured with time using a Benchmark Plus microplate spectrophotometer (from BIO-RAD). Samples in which NADPH was consumed due to the reduction of 2,3-butadione and thus fluorescence was quenched were selected as recombinant bacteria with altered carbonyl reductases having even better resistance to the reaction inhibition by an organic solvent. Plasmids were extracted from the culture media of the selected recombinant bacteria, and the base sequence of the mutant RKP genes was determined using BigDye Terminator Cycle Sequencing Kit (from Applied Biosystems Japan, Ltd.) and Applied Biosystems 3130xl Genetic Analyzer (from Applied Biosystems Japan, Ltd.), whereby the mutation sites were identified. The obtained altered carbonyl reductases having better resistance to the reaction inhibition by an organic solvent are shown in Table 8.

TABLE 8

| Plasmid | Mutation site |
| --- | --- |
| pNKPm51 | K22R-F87I-K259E-K270M |
| pNKPm52 | D90G-K259E-K270M |
| pNKPm53 | K39R-T51A-K259E-K270M |

The three enzymes shown in Table 8 having better resistance to the reaction inhibition by an organic solvent were obtained.

(Example 31) Evaluation 3 of Altered Carbonyl Reductase

The recombinant bacteria with the altered carbonyl reductases obtained in Example 30 and *E. coli* HB101 (pNKP) (control) prepared in Reference Example 3 were each cultured in the same manner as in Reference Example 4. The cells in the obtained culture media were collected by centrifugation and suspended in 100 mM phosphate buffer (pH 6.5) in an amount of ⅕ of the amount of the culture medium. The suspension was disrupted with a model UH-50 ultrasonic homogenizer (from SMT), followed by removing the cell debris by centrifugation to obtain a cell-free extract. An amount of 100 μL of each of the cell-free extracts was mixed with 400 μL of 1M phosphate buffer (pH 7.0), 500 μL of water or a 60% DMF solution, 1% 2-hexanone, 5% NADPH, and 3.4% glucose. The mixture was reacted with stirring at 30° C. for 2 hours. After the reaction, the reaction mixture was extracted with ethyl acetate. The thus obtained extracts were analyzed under the conditions described below in "Analysis conditions for gas chromatography" to determine the production of 2-hexanol. Conversion ratio was calculated from the peak areas of 2-hexanol and 2-hexanone.

[Analysis Conditions for Gas Chromatography]

Column: InertCapI capillary column (30 m, inner diameter: 0.25 mm, product of GL Sciences)
Detector: hydrogen flame ionization detector
Injection site temperature: 250° C.
Column temperature: 50° C.
Detector temperature: 250° C.
Carrier gas: helium, flow rate=150 kPa From the conversion ratio, the relative activity of the recombinant bacteria in the presence of 60% dimethylformamide compared to the activity in the absence of dimethylformamide was calculated. The relative activity was calculated by the equation below and used as an indicator of reaction inhibition by dimethylformamide. The results are shown in Table 9.

Relative activity (%)=[conversion ratio in the presence of dimethylformamide]/[conversion ratio in the absence of dimethylformamide]×100

The altered carbonyl reductases having better resistance to the reaction inhibition by an organic solvent are shown in Table 9.

TABLE 9

| Mutation site | Residual activity (%) |
| --- | --- |
| Wild-type enzyme | 24 |
| K22R-F87I-K259E-K270M | 35 |
| D90G-K259E-K270M | 31 |
| K39R-T51A-K259E-K270M | 31 |

The three enzymes shown in Table 9 having better resistance to the reaction inhibition by an organic solvent were obtained. The altered carbonyl reductases shown in the table had better resistance to the reaction inhibition by dimethylformamide, which is an organic solvent, than the wild-type enzyme.

(Example 32) Production of 3-[(5R)-(4-fluoro-phenyl)-5-hydroxypentanoyl]-(4S)-phenyl-1,3-oxazolidin-2-one To 700 μL of the culture of the recombinant *E. coli* expressing the carbonyl reductase RKP (wild-type) derived from *Vanderwaltozyma polyspora* NBRC0996 obtained in Reference Example 4 or a culture obtained by culturing the recombinant *E. coli* producing the altered carbonyl reductase T257S-K259E-K270M obtained in Example 24 in the same manner as in Reference Example 4 were added glucose dehydrogenase (trade name: GLUCDH "Amano" II, product of Amano Enzyme Inc., 12.5 U), 80 mg of glucose, 0.6 mg of NADP$^+$, 300 μL of dimethylformamide or 0.1 M phosphate buffer (pH 7), and 10 mg of (S)-1-(4-fluoro-phenyl)-

5-(2-oxo-4-phenyl-oxazolidin-3-yl)-pentane-1,5-dione, and the mixture was stirred at 30° C. for 20 hours. The reaction mixture was diluted with dimethyl sulfoxide and analyzed by high-speed liquid chromatography under the conditions described below to determine the conversion ratio to 3-(5R)-(4-fluoro-phenyl)-5-hydroxypentanoyl]-(4S)-phenyl-1,3-oxazolidin-2-one and the optical purity thereof. The results are shown in Table 10.

TABLE 10

| Enzyme | DMF concentration (%) | Conversion ratio (%) | Optical purity of S-form (% e.e) |
|---|---|---|---|
| Wild-type | 0 | 54.4 | 89.21 |
| Wild-type | 30 | 16.6 | 87.89 |
| T257S-K259E-K270M | 0 | 47.5 | 80.15 |
| T257S-K259E-K270M | 30 | 99.0 | 73.91 |

Method for Calculation and Analysis Conditions of Conversion Ratio to 3-(5R)-(4-fluoro-phenyl)-5-hydroxypentanoyl]-(4S)-phenyl-1,3-oxazolidin-2-one Column: COSMOSIL 5C8-MS (250 mm, inner diameter: 4.6 μm, product of Nacalai Tesque, Inc.)
Column temperature: 40° C.
Detection wavelength: 254 mm
Mobile phase: water/acetonitrile=1/1
Retention time: [3-[(5)-(4-fluoro-phenyl)-5-hydroxypentanoyl]-(4)-phenyl-1,3-oxazolidin-2-one=about 8.5 minutes, 1-(4-fluoro-phenyl)-5-(2-oxo-4-phenyl-oxazolidin-3-yl)-pentane-1,5-dione=about 12.9 minutes Conversion ratio=[produced amount of 3-[(5)-(4-fluoro-phenyl)-5-hydroxypentanoyl]-(4)-phenyl-1,3-oxazolidin-2-one]/[(produced amount of 3-[(5)-(4-fluoro-phenyl)-5-hydroxypentanoyl]-(4)-phenyl-1,3-oxazolidin-2-one)+(residual amount of 1-(4-fluoro-phenyl)-5-(2-oxo-4-phenyl-oxazolidin-3-yl)-pentane-1,5-dione)]×100

Method for Calculation and Analysis Conditions of Optical Purity of 3-[(5R)-(4-fluoro-phenyl)-5-hydroxypentanoyl]-(4S)-phenyl-1,3-oxazolidin-2-one Column: CHIRALCEL OD-H (250 mm, inner diameter: 4.6 μm, Daicel Chemical Industries, Ltd.)
Column temperature: 30 C.°
Detection wavelength: 254 mm
Mobile phase: hexane/ethanol=8/2
Retention time: 3-[(5R)-(4-fluoro-phenyl)-5-hydroxypentanoyl]-(4S)-phenyl-1,3-oxazolidin-2-one=about 18.1 minutes, 3-[(5S)-(4-fluoro-phenyl)-5-hydroxypentanoyl]-(4S)-phenyl-1,3-oxazolidin-2-one=about 21.7 minutes Optical purity of R-form (% e.e.)={(peak area of R-form)−(peak area of S-form)}/{(peak area of R-form)+(peak area of S-form)}×100

---

The invention claimed is:

1. An altered carbonyl reductase having the following properties (a) to (c):
   (a) an amino acid sequence having at least 85% sequence identity to the amino acid sequence of SEQ ID NO:1;
   (b) reduces 2-pentanone into 2-pentanol;
   (c) higher activity to reduce carbonyl compound in the presence of an organic solvent compared to the activity of the carbonyl reductase of SEQ ID NO:1 wherein the organic solvent is dimethylformamide, and wherein the altered carbonyl reductase comprises an amino acid substitution, relative to the amino acid sequence of SEQ ID NO:1, at one or more positions selected from the group consisting of positions 2, 22, 25, 39, 42, 45, 51, 56, 71, 87, 90, 102, 109, 124, 135, 138, 155, 159, 175, 177, 183, 190, 195, 212, 220, 226, 228, 236, 238, 250, 254, 257, 259, 265, 267, 270, 279, 298, 300, 301 and 331.

2. The altered carbonyl reductase according to claim 1, wherein the amino acid substitution is one or more of the following amino acid substitutions relative to the amino acid sequence of SEQ ID NO:1:
   substitutions at position 2 with isoleucine, at position 22 with arginine, at position 25 with phenylalanine, at position 39 with arginine, at position 42 with arginine, at position 45 with aspartic acid, at position 51 with alanine, at position 56 with lysine, at position 71 with asparagine or arginine, at position 87 with isoleucine, at position 90 with glycine, at position 102 with isoleucine, at position 109 with glycine, at position 124 with leucine, at position 135 with alanine, at position 138 with asparagine, at position 155 with leucine or arginine, at position 159 with phenylalanine, at position 175 with aspartic acid, at position 177 with phenylalanine, at position 183 with threonine, at position 190 with serine, at position 195 with leucine, at position 212 with phenylalanine, threonine, or tyrosine, at position 220 with valine, at position 226 with glycine, at position 228 with valine, at position 236 with asparagine, at position 238 with isoleucine, at position 250 with proline, at position 254 with asparagine, at position 257 with serine, at position 259 with glutamic acid, at position 265 with lysine, at position 267 with proline, at position 270 with methionine, at position 279 with arginine, at position 298 with proline, at position 300 with aspartic acid, at position 301 with cysteine, and at position 331 with phenylalanine.

3. The altered carbonyl reductase according to claim 2, wherein the amino acid substitution is one or more of the following amino acid substitutions relative to the amino acid sequence of SEQ ID NO: 1:
   substitutions at position 2 with isoleucine, at position 45 with aspartic acid, at position 71 with asparagine or arginine, at position 102 with isoleucine, at position 124 with leucine, at position 175 with aspartic acid, at position 177 with phenylalanine, at position 183 with threonine, at position 195 with leucine, at position 220 with valine, at position 226 with glycine, at position 236 with asparagine, at position 238 with isoleucine, at position 257 with serine, at position 259 with glutamic acid, at position 265 with lysine, at position 267 with proline, at position 270 with methionine, at position 300 with aspartic acid, and at position 301 with cysteine, and
the altered carbonyl reductase has higher stability than the wild-type carbonyl reductase of SEQ ID NO:1 when the residual activity toward 2-pentanone or 2-hexanone of the carbonyl reductase after incubation with dimethylformamide is measured, the enzyme has a higher residual activity than the wild-type enzyme by at least 1% to the organic solvent than the carbonyl reductase comprising the amino acid sequence of SEQ ID NO:1.

4. The altered carbonyl reductase according to claim 3, wherein the amino acid substitution is selected from the following amino acid substitutions (1) to (35) relative to the amino acid sequence of SEQ ID NO:1:
   (1) an amino acid substitution at position 71 with asparagine and at position 195 with leucine;
   (2) an amino acid substitution at position 71 with arginine and at position 259 with glutamic acid;
   (3) an amino acid substitution at position 71 with arginine and at position 270 with methionine;
   (4) an amino acid substitution at position 71 with arginine and at position 300 with aspartic acid;
   (5) an amino acid substitution at position 102 with isoleucine and at position 270 with methionine;
   (6) an amino acid substitution at position 177 with phenylalanine and at position 220 with valine;
   (7) an amino acid substitution at position 226 with glycine and at position 270 with methionine;
   (8) an amino acid substitution at position 257 with serine and at position 259 with glutamic acid;
   (9) an amino acid substitution at position 257 with serine and at position 270 with methionine;
   (10) an amino acid substitution at position 259 with glutamic acid and at position 270 with methionine;
   (11) an amino acid substitution at position 259 with glutamic acid and at position 300 with aspartic acid;
   (12) an amino acid substitution at position 267 with proline and at position 270 with methionine;
   (13) an amino acid substitution at position 270 with methionine and at position 300 with aspartic acid;
   (14) an amino acid substitution at position 2 with isoleucine, at position 259 with glutamic acid, and at position 270 with methionine;

(15) an amino acid substitution at position 45 with aspartic acid, at position 175 with aspartic acid, and at position 183 with threonine;
(16) an amino acid substitution at position 102 with isoleucine, at position 226 with glycine, and at position 267 with proline;
(17) an amino acid substitution at position 124 with leucine, at position 259 with glutamic acid, and at position 270 with methionine;
(18) an amino acid substitution at position 177 with phenylalanine, at position 259 with glutamic acid, and at position 270 with methionine;
(19) an amino acid substitution at position 220 with valine, at position 259 with glutamic acid, and at position 270 with methionine;
(20) an amino acid substitution at position 236 with asparagine, at position 259 with glutamic acid, and at position 270 with methionine;
(21) an amino acid substitution at position 238 with isoleucine, at position 259 with glutamic acid, and at position 270 with methionine;
(22) an amino acid substitution at position 257 with serine, at position 259 with glutamic acid, and at position 270 with methionine;
(23) an amino acid substitution at position 257 with serine, at position 259 with glutamic acid, and at position 300 with aspartic acid;
(24) an amino acid substitution at position 259 with glutamic acid, at position 265 with lysine, and at position 270 with methionine;
(25) an amino acid substitution at position 259 with glutamic acid, at position 270 with methionine, and at position 300 with aspartic acid;
(26) an amino acid substitution at position 259 with glutamic acid, at position 270 with methionine, and at position 301 with cysteine;
(27) an amino acid substitution at position 2 with isoleucine and at position 238 with isoleucine;
(28) an amino acid substitution at position 71 with asparagine and at position 195 with leucine;
(29) an amino acid substitution at position 109 with glycine and at position 331 with phenylalanine;
(30) an amino acid substitution at position 124 with leucine and at position 236 with asparagine;
(31) an amino acid substitution at position 159 with phenylalanine and at position 259 with glutamic acid;
(32) an amino acid substitution at position 42 with arginine, at position 155 with arginine, and at position 279 with arginine;
(33) an amino acid substitution at position 45 with aspartic acid, at position 175 with aspartic acid, and at position 183 with threonine;
(34) an amino acid substitution at position 155 with leucine, at position 250 with proline, and at position 298 with proline; and
(35) an amino acid substitution at position 56 with lysine, at position 138 with asparagine, at position 190 with serine, and at position 254 with asparagine.

5. The altered carbonyl reductase according to claim 2, wherein the amino acid substitution is one or more of the following amino acid substitutions:

substitutions at position 22 with arginine, at position 39 with arginine, at position 51 with alanine, at position 87 with isoleucine, at position 90 with glycine, at position 259 with glutamic acid, and at position 270 with methionine, and the altered carbonyl reductase has better resistance when the relative activity toward 2-hexanone in the presence of dimethylformamide is measured, the enzyme has higher relative activity than the wild-type enzyme by at least 1% to reaction inhibition by the organic solvent than the carbonyl reductase comprising the amino acid sequence of SEQ ID NO:1.

6. The altered carbonyl reductase according to claim 5, wherein the amino acid substitution is one or more of the following amino acid substitutions (1) to (7) relative to the amino acid sequence of SEQ ID NO:1:
(1) an amino acid substitution at position 22 with arginine;
(2) an amino acid substitution at position 22 with arginine and at position 87 with isoleucine;
(3) an amino acid substitution at position 39 with arginine;
(4) an amino acid substitution at position 39 with arginine and at position 51 with alanine;
(5) an amino acid substitution at position 51 with alanine;
(6) an amino acid substitution at position 87 with isoleucine; and
(7) an amino acid substitution at position 90 with glycine.

7. The altered carbonyl reductase of claim 1, wherein the altered carbonyl reductase has an amino acid sequence having at least 90% sequence identity to the amino acid sequence of SEQ ID NO:1.

* * * * *